United States Patent
Wu et al.

(10) Patent No.: US 12,270,022 B2
(45) Date of Patent: Apr. 8, 2025

(54) PICHIA PASTORIS MUTANT STRAIN FOR EXPRESSING EXOGENOUS GENE

(71) Applicant: WILMAR (SHANGHAI) BIOTECHNOLOGY RESEARCH & DEVELOPMENT CENTER CO., LTD, Shanghai (CN)

(72) Inventors: Wei Wu, Shanghai (CN); Xiaojun Dai, Shanghai (CN); Haisheng Cao, Shanghai (CN); Meifeng Zhou, Jiaxing (CN); Qiwen Niu, Shanghai (CN)

(73) Assignee: WILMAR (SHANGHAI) BIOTECHNOLOGY RESEARCH & DEVELOPMENT CENTER CO., LTD., Shanghai (CN)

( * ) Notice: Subject to any disclaimer, the term of this patent is extended or adjusted under 35 U.S.C. 154(b) by 875 days.

(21) Appl. No.: 17/419,122

(22) PCT Filed: Dec. 27, 2019

(86) PCT No.: PCT/CN2019/129359
§ 371 (c)(1),
(2) Date: Jun. 28, 2021

(87) PCT Pub. No.: WO2020/135763
PCT Pub. Date: Jul. 2, 2020

(65) Prior Publication Data
US 2022/0162543 A1    May 26, 2022

(51) Int. Cl.
| C12N 1/16 | (2006.01) |
| C12N 9/16 | (2006.01) |
| C12N 15/81 | (2006.01) |
| C12P 7/649 | (2022.01) |
| C12R 1/84 | (2006.01) |

(52) U.S. Cl.
CPC ............... *C12N 1/165* (2021.05); *C12N 9/16* (2013.01); *C12N 15/815* (2013.01); *C12P 7/649* (2013.01); *C12R 2001/84* (2021.05)

(58) Field of Classification Search
CPC ........ C12N 1/165; C12N 9/16; C12N 15/815; C12N 9/0036; C12N 9/88; C12N 9/20; C12N 9/52; C12N 1/16; C12N 9/18; C12N 9/2411; C12N 9/2437; C12N 9/2465; C12N 9/50; C12P 7/649; C12R 2001/84; A23K 20/147; A23K 20/189; A23L 29/06; A23L 33/14; A23L 33/195; C07K 14/39; C11B 3/003; C11C 3/10; C12Y 106/05; C12Y 106/0501; C12Y 401/01023; C12Y 301/01003; C12Y 302/01004

See application file for complete search history.

(56) References Cited

U.S. PATENT DOCUMENTS

2004/0152180 A1    8/2004    Minning et al.

FOREIGN PATENT DOCUMENTS

| CN | 86107108 A | 6/1987 | |
| CN | 1484693 A | 3/2004 | |
| CN | 106047732 A | 10/2016 | |
| CN | 106884009 A | 6/2017 | |
| CN | 108239627 A | 7/2018 | |
| CN | 108239648 A | 7/2018 | |
| CN | 109957520 A | 7/2019 | |
| DE | 1788080 A1 * | 5/2007 | ............... C12N 9/20 |
| EP | 0180899 A2 | 5/1986 | |
| EP | 3392336 A1 | 10/2018 | |
| JP | 2017-511148 A | 4/2017 | |
| WO | WO 2003060112 A1 * | 7/2003 | ............... C12N 9/20 |
| WO | 2014/066374 A1 | 5/2014 | |
| WO | 2015/158808 A2 | 10/2015 | |

OTHER PUBLICATIONS

Boel et al., "Rhizomucor miehei triglyceride lipase is synthesized as a precursor", Lipids, 1988, vol. 23 (7), pp. 701-706. (Year: 1988).*
Liu et al., Streptomyces violaceoruber phospholipase A2: expression in Pichia pastoris, properties, and application in oil degumming. Appl Biochem Biotechnol. Mar. 2015;175(6):3195-206.
GenBank Accession No. WP_048557546, phospholipase CerA [*Bacillus cereus* group sp. BY9-3LC]. 2 pages, May 6, 2023.
GenPepl Accession No. 1DT3_A, Chain A, Lipase. 2 pages, Dec. 1, 2020.
International Search Report and Written Opinion for Application No. PCT/CN2019/129359, dated Mar. 27, 2020, 22 pages.

* cited by examiner

*Primary Examiner* — Satyendra K Singh
(74) *Attorney, Agent, or Firm* — McCarter & English, LLP; David R. Burns; Maneesh Gulati

(57) ABSTRACT

Provided is a *Pichia pastoris* mutant strain for expressing an exogenous gene. Specifically, provided is a *Pichia pastoris* mutant strain comprising, with respect to *Pichia pastoris* mutant strain GS115 or CICC32806, one or more of the following six mutations: BQ9382_C1-2260, EKK deletions at positions 308-310, a hypothetical protein; BQ9382_C1-3800, E129K, 60S ribosomal subunit assembly/exported protein LOC1; BQ9382_C1-5700, 1312M, mitochondrial external NADH dehydrogenase, type II NAD(P)H: quinone oxidoreductase; BQ9382_C2-3950, Q145X, an essential protein having a binding partner Psr1p and used for completely activating a general stress response; BQ9382_C3-2220, E188K, a hypothetical protein; and BQ9382_C3-4370, W196X, orotidine 5\'-phosphate decarboxylase. The provided *Pichia pastoris* mutant strain is an effective commonly employed host for exogenous expression, and can efficiently express different proteins, especially phospholipase and lipase.

14 Claims, 4 Drawing Sheets
Specification includes a Sequence Listing.

SEQUENCE LISTING

<160> NUMBER OF SEQ ID NOS: 32

<210> SEQ ID NO 1
<211> LENGTH: 1005
<212> TYPE: DNA
<213> ORGANISM: Artificial Sequence
<220> FEATURE:
<223> OTHER INFORMATION: synthetic polynucleotide encoding phospholipase
      C

<400> SEQUENCE: 1

```
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc catttccaa cagcacaaat      180 aacgggttat tgtttataaa tactactatt gccagcattg ctgctaaaga agaagggta      240 tctcttgaga aagagaggc tgaagcttgg tcagctgagg acaagcataa ggaaggtgtg      300
aatagtcact tatggatcgt gaaccgtgcc attgatataa tgtctaggaa tacaactctg      360
gttaagcaag atagagttgc tcaattgaat gaatggcgta cagagctaga gaatggcatc      420
tacgctgctg attatgaaaa ccctattac gataacagta ccttcgcttc tcacttttac       480
gatccagaca acggaaagac atatatccca ttcgccaagc aagctaagga gactggagct     540
```

-continued

```
aagtacttca agttggctgg agagtcatac aagaataaag acatgaagca ggccttcttt    600
tatcttgggt tgtcattgca ttatttgggc gatgtcaacc aacctatgca tgccgcaaac    660
tttacgaacc tgtcctatcc acagggtttt cactccaagt acgagaactt tgtcgatact    720
attaaagaca actacaaagt taccgatggg aacggatatt ggaattggaa aggcaccaac    780
cctgaagaat ggattcacgg tgcagcagta gttgcaaaac aggactactc tggaattgtc    840
aatgacaata ccaaagattg gtttgtgaaa gccgcagtct cccaggaata tgcagataaa    900
tggagagctg aagttacacc tatgactggt aaacgactaa tggatgccca aagagttact    960
gctggttaca ttcaattatg gttcgacact tacggtgaca ggtaa                   1005
```

<210> SEQ ID NO 2
<211> LENGTH: 334
<212> TYPE: PRT
<213> ORGANISM: Artificial Sequence
<220> FEATURE:
<223> OTHER INFORMATION: synthetic phospholipase C

<400> SEQUENCE: 2

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Trp Ser Ala Glu Asp Lys His
                85                  90                  95

Lys Glu Gly Val Asn Ser His Leu Trp Ile Val Asn Arg Ala Ile Asp
            100                 105                 110

Ile Met Ser Arg Asn Thr Thr Leu Val Lys Gln Asp Arg Val Ala Gln
        115                 120                 125

Leu Asn Glu Trp Arg Thr Glu Leu Glu Asn Gly Ile Tyr Ala Ala Asp
    130                 135                 140

Tyr Glu Asn Pro Tyr Tyr Asp Asn Ser Thr Phe Ala Ser His Phe Tyr
145                 150                 155                 160

Asp Pro Asp Asn Gly Lys Thr Tyr Ile Pro Phe Ala Lys Gln Ala Lys
                165                 170                 175

Glu Thr Gly Ala Lys Tyr Phe Lys Leu Ala Gly Glu Ser Tyr Lys Asn
            180                 185                 190

Lys Asp Met Lys Gln Ala Phe Phe Tyr Leu Gly Leu Ser Leu His Tyr
        195                 200                 205

Leu Gly Asp Val Asn Gln Pro Met His Ala Ala Asn Phe Thr Asn Leu
    210                 215                 220

Ser Tyr Pro Gln Gly Phe His Ser Lys Tyr Glu Asn Phe Val Asp Thr
225                 230                 235                 240

Ile Lys Asp Asn Tyr Lys Val Thr Asp Gly Asn Gly Tyr Trp Asn Trp
                245                 250                 255

Lys Gly Thr Asn Pro Glu Glu Trp Ile His Gly Ala Ala Val Val Ala
            260                 265                 270

Lys Gln Asp Tyr Ser Gly Ile Val Asn Asp Asn Thr Lys Asp Trp Phe
        275                 280                 285
```

```
Val Lys Ala Ala Val Ser Gln Glu Tyr Ala Asp Lys Trp Arg Ala Glu
    290                 295                 300

Val Thr Pro Met Thr Gly Lys Arg Leu Met Asp Ala Gln Arg Val Thr
305                 310                 315                 320

Ala Gly Tyr Ile Gln Leu Trp Phe Asp Thr Tyr Gly Asp Arg
                325                 330
```

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3

| | |
|---|---:|
| tacgtatggt cagctgagga caagc | 25 |

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4

| | |
|---|---:|
| cctaggttac ctgtcaccgt aagtgtcgaa | 30 |

<210> SEQ ID NO 5
<211> LENGTH: 1817
<212> TYPE: DNA
<213> ORGANISM: Artificial Sequence
<220> FEATURE:
<223> OTHER INFORMATION: synthetic construct

<400> SEQUENCE: 5

| | |
|---|---:|
| ctcgagattc aggtgaaccc acctaactat ttttaactgg gatccagtga gctcgctggg | 60 |
| tgaaagccaa ccatctttg tttcggggaa ccgtgctcgc ccgtaaagt taatttttt | 120 |
| ttcccgcgca gctttaatct ttcggcagag aaggcgtttt catcgtagcg tgggaacaga | 180 |
| ataatcagtt catgtgctat acaggcacat ggcagcagtc actattttgc ttttaacct | 240 |
| taaagtcgtt catcaatcat taactgacca atcagatttt ttgcatttgc cacttatcta | 300 |
| aaaatacttt tgtatctcgc agatacgttc agtggtttcc aggacaacac ccaaaaaaag | 360 |
| gtatcaatgc cactaggcag tcggttttat ttttggtcac ccacgcaaag aagcacccac | 420 |
| ctctttagg ttttaagttg tgggaacagt aacaccgcct agagcttcag gaaaaaccag | 480 |
| tacctgtgac cgcaattcac catgatgcag aatgttaatt taaacgagtg ccaaatcaag | 540 |
| atttcaacag acaaatcaat cgatccatag ttacccattc cagccttttc gtcgtcgagc | 600 |
| ctgcttcatt cctgcctcag gtgcataact ttgcatgaaa agtccagatt agggcagatt | 660 |
| ttgagtttaa ataggaaat ataaacaat ataccgcgaa aaaggtttgt ttatagcttt | 720 |
| tcgcctggtg ccgtacggta taaatacata ctctcctccc ccccctggtt ctcttttct | 780 |
| tttgttactt acatttttacc gttccgtcac tcgcttcact caacaacaaa ataaactagt | 840 |
| ggtaccgtca gccaccaaag tagtgaatag accatcgggg cggtcagtag tcaaagacgc | 900 |
| caacaaaatt tcactgacag ggaacttttt gacatcttca gaaagttcgt attcagtagt | 960 |
| caattgccga gcatcaataa tggggattat accagaagca acagtggaag tcacatctac | 1020 |
| caactttgcg gtctcagaaa aagcataaac agttctacta ccgccattag tgaaactttt | 1080 |

```
caaatcgccc agtggagaag aaaaaggcac agcgatacta gcattagcgg gcaaggatgc   1140
aactttatca accagggtcc tatagataac cctagcgcct gggatcatcc tttggacaac   1200
tctttctgcc aaatctaggt ccaaaatcac ttcattgata ccattattgt acaacttgag   1260
caagttgtcg atcagctcct caaattggtc tctgtaacg dgatgactcaa cttgcacatt    1320 aacttgaagc tcagtcgatt gagtgaactt gatcaggttg tgcagctggt cagcagcata   1380
gggaaacacg gcttttccta ccaaactcaa ggaattatca aactctgcaa cacttgcgta   1440
tgcaggtagc aagggaaatg tcatacttga agtcggacag tgagtgtagt cttgagaaat   1500
tctgaagccg tattttattt atcagtgagt cagtcatcag gagatcctct acgccggacg   1560
catcgtggcc ggcatcaccg gcgccacagg tgcggttgct ggcgcctata tcgccgacat   1620
caccgatggg gaagatcggg ctcgccactt cgggctcatg agcgcttgtt tcggcgtggg   1680
tatggtggca ggccccgtgg ccggggggact gttgggcgcc atctccttgc atgcaccatt   1740
ccttgcggcg gcggtgctca acggcctcaa cctactactg ggctgcttcc taatgcagga   1800
gtcgcataag ggaattc                                                 1817
```

```
<210> SEQ ID NO 6
<211> LENGTH: 1038
<212> TYPE: DNA
<213> ORGANISM: Artificial Sequence
<220> FEATURE:
<223> OTHER INFORMATION: synthetic polynucleotide encoding RML lipase

<400> SEQUENCE: 6
```

```
gttccaatca agagacaatc taattccact gtcgattctt tgcctccatt gattccttct     60
agaactagtg caccttcatc ctctccatct acaactgacc ctgaggctcc agctatgtca    120
agaaatggtc cacttccttc tgatgttgag accaagtacg gaatggccct gaatgctact    180
tcttatccag attctgtcgt tcaagctatg aaaagagagg ctgaagcttc catcgacgga    240
ggtattagag ccgctacttc tcaggaaatc aacgaactta cttactatac aactttgtca    300
gctaattctt actgtagaac tgttattcct ggtgctactt gggattgcat acattgtgac    360
gccactgaag atttaaagat aattaaaacc tggtctactt tgatttacga cactaacgct    420
atggttgcta gaggagattc cgagaagact atttatatcg tgtttagagg ttcttcatct    480
attcgtaatt ggatcgctga tttgacattc gttccagtct cttaccctcc agttctggt    540 actaaggttc acaaaggatt tcttgattct tatggtgaag ttcaaaacga gttggttgct    600
actgtcttgg atcagtttaa acaatacccca tcttataagg ttgctgtcac tggtcactct    660
ttgggaggtg ctactgcctt gctgtgtgct ttaggtttat accagagaga ggaaggattg    720
tcttcaagta acctattctt gtacactcaa ggtcagccta gagttggaga tccagcattt    780
gctaattatg tggttctac tggtattcca tatagacgta ctgttaacga aagagacata    840
gtaccacact gcctccagc tgccttcgga tttctgcatg ccggtgaaga gtactggatc    900
acagataatt ctcctgaaac cgttcaagtg tgtacatctg atttagagac ttccgactgc    960
tctaacagta ttgttccatt tacttcagtt cttgatcatt tgtcttattt tggaattaac   1020
accggtttgt gtacttaa                                                1038
```

```
<210> SEQ ID NO 7
<211> LENGTH: 345
<212> TYPE: PRT
<213> ORGANISM: Artificial Sequence
<220> FEATURE:
```

<223> OTHER INFORMATION: synthetic RML lipase

<400> SEQUENCE: 7

| | | | | | | | | | | | | | | |
|---|---|---|---|---|---|---|---|---|---|---|---|---|---|---|
| Val | Pro | Ile | Lys | Arg | Gln | Ser | Asn | Ser | Thr | Val | Asp | Ser | Leu | Pro | Pro |
| 1 | | | | 5 | | | | | 10 | | | | | 15 | |
| Leu | Ile | Pro | Ser | Arg | Thr | Ser | Ala | Pro | Ser | Ser | Pro | Ser | Thr | Thr |
| | | | 20 | | | | | 25 | | | | | 30 | |
| Asp | Pro | Glu | Ala | Pro | Ala | Met | Ser | Arg | Asn | Gly | Pro | Leu | Pro | Ser | Asp |
| | | 35 | | | | | 40 | | | | | 45 | | | |
| Val | Glu | Thr | Lys | Tyr | Gly | Met | Ala | Leu | Asn | Ala | Thr | Ser | Tyr | Pro | Asp |
| | 50 | | | | | 55 | | | | | 60 | | | | |
| Ser | Val | Val | Gln | Ala | Met | Lys | Arg | Glu | Ala | Glu | Ala | Ser | Ile | Asp | Gly |
| 65 | | | | | 70 | | | | | 75 | | | | | 80 |
| Gly | Ile | Arg | Ala | Ala | Thr | Ser | Gln | Glu | Ile | Asn | Glu | Leu | Thr | Tyr | Tyr |
| | | | | 85 | | | | | 90 | | | | | 95 | |
| Thr | Thr | Leu | Ser | Ala | Asn | Ser | Tyr | Cys | Arg | Thr | Val | Ile | Pro | Gly | Ala |
| | | | 100 | | | | | 105 | | | | | 110 | | |
| Thr | Trp | Asp | Cys | Ile | His | Cys | Asp | Ala | Thr | Glu | Asp | Leu | Lys | Ile | Ile |
| | | | 115 | | | | | 120 | | | | | 125 | | |
| Lys | Thr | Trp | Ser | Thr | Leu | Ile | Tyr | Asp | Thr | Asn | Ala | Met | Val | Ala | Arg |
| 130 | | | | | 135 | | | | | 140 | | | | | |
| Gly | Asp | Ser | Glu | Lys | Thr | Ile | Tyr | Ile | Val | Phe | Arg | Gly | Ser | Ser | Ser |
| 145 | | | | | 150 | | | | | 155 | | | | | 160 |
| Ile | Arg | Asn | Trp | Ile | Ala | Asp | Leu | Thr | Phe | Val | Pro | Val | Ser | Tyr | Pro |
| | | | | 165 | | | | | 170 | | | | | 175 | |
| Pro | Val | Ser | Gly | Thr | Lys | Val | His | Lys | Gly | Phe | Leu | Asp | Ser | Tyr | Gly |
| | | | 180 | | | | | 185 | | | | | 190 | | |
| Glu | Val | Gln | Asn | Glu | Leu | Val | Ala | Thr | Val | Leu | Asp | Gln | Phe | Lys | Gln |
| | | | 195 | | | | | 200 | | | | | 205 | | |
| Tyr | Pro | Ser | Tyr | Lys | Val | Ala | Val | Thr | Gly | His | Ser | Leu | Gly | Gly | Ala |
| | | 210 | | | | | 215 | | | | | 220 | | | |
| Thr | Ala | Leu | Leu | Cys | Ala | Leu | Gly | Leu | Tyr | Gln | Arg | Glu | Glu | Gly | Leu |
| 225 | | | | | 230 | | | | | 235 | | | | | 240 |
| Ser | Ser | Ser | Asn | Leu | Phe | Leu | Tyr | Thr | Gln | Gly | Gln | Pro | Arg | Val | Gly |
| | | | | 245 | | | | | 250 | | | | | 255 | |
| Asp | Pro | Ala | Phe | Ala | Asn | Tyr | Val | Val | Ser | Thr | Gly | Ile | Pro | Tyr | Arg |
| | | | 260 | | | | | 265 | | | | | 270 | | |
| Arg | Thr | Val | Asn | Glu | Arg | Asp | Ile | Val | Pro | His | Leu | Pro | Pro | Ala | Ala |
| | | 275 | | | | | 280 | | | | | 285 | | | |
| Phe | Gly | Phe | Leu | His | Ala | Gly | Glu | Glu | Tyr | Trp | Ile | Thr | Asp | Asn | Ser |
| | 290 | | | | | 295 | | | | | 300 | | | | |
| Pro | Glu | Thr | Val | Gln | Val | Cys | Thr | Ser | Asp | Leu | Glu | Thr | Ser | Asp | Cys |
| 305 | | | | | 310 | | | | | 315 | | | | | 320 |
| Ser | Asn | Ser | Ile | Val | Pro | Phe | Thr | Ser | Val | Leu | Asp | His | Leu | Ser | Tyr |
| | | | | 325 | | | | | 330 | | | | | 335 | |
| Phe | Gly | Ile | Asn | Thr | Gly | Leu | Cys | Thr |
| | | | 340 | | | | | 345 |

<210> SEQ ID NO 8
<211> LENGTH: 810
<212> TYPE: DNA
<213> ORGANISM: Artificial Sequence
<220> FEATURE:
<223> OTHER INFORMATION: synthetic polynucleotide encoding TL lipase

<400> SEQUENCE: 8

```
gaagtctctc aagacttgtt caaccagttc aacttgttcg ctcaatactc tgccgctgcc    60
tactgtggta agaacaatga tgctccagct ggtactaaca ttacctgtac tggtaacgct   120
tgtccagaag ttgagaaggc tgatgctacc ttcctgtact ccttcgaaga ctctggagtt   180
ggagatgtta ctggtttcct ggccttggat aacactaaca agttgatcgt tctgtccttc   240
agaggttcca gatccatcga aactggattg gtaacttga actttgactt gaaggagatc   300
aacgacatct gttctggatg tcgtggtcac gatggattta cctcctcttg gagatctgtt   360
gctgataccct tgagacagaa ggtcgaagat gctgtcagag aacatccaga ctatagagtt   420
gtcttcactg gtcactcctt gggaggtgcc ttggctactg ttgctggtgc tgacttgcgt   480
ggtaatggtt atgacattga tgtcttctcc tacggtgctc aagagttgg taatcgtgcc   540
ttcgctgagt ttctgaccgt ccaaactgga ggtactttgt acagaattac ccatactaac   600
gacattgttc caagattgcc accacgtgag ttcggatact ctcattcctc tccagagtac   660
tggatcaagt ctggaacctt ggttccagtc actcgtaacg acatcgtcaa gattgaaggt   720
attgatgcca ctggaggtaa caatcaacca acattccag acattccagc tcacttgtgg   780
tactttggtc tgattggtac ttgcttgtaa                                    810
```

<210> SEQ ID NO 9
<211> LENGTH: 269
<212> TYPE: PRT
<213> ORGANISM: Artificial Sequence
<220> FEATURE:
<223> OTHER INFORMATION: synthetic TL lipase

<400> SEQUENCE: 9

```
Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205
```

```
Arg Glu Phe Gly Tyr Ser His Ser Ser Pro Glu Tyr Trp Ile Lys Ser
            210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265
```

```
<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
ccgctcgagt cacctcagcc agatcaaagt                                     30

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
acatgcatgc ctttggacaa ctctttctgc c                                   31

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
cggggtaccc ctggttgata aagttgcat                                      29

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
ggcgagctca ggtgtcttca aagcgactc                                      29

<210> SEQ ID NO 14
<211> LENGTH: 35
<212> TYPE: DNA
<213> ORGANISM: Artificial Sequence
<220> FEATURE:
<223> OTHER INFORMATION: primer

<400> SEQUENCE: 14
acatgcatgc ctgcagaaat ggggagataa ccacc                               35

<210> SEQ ID NO 15
<211> LENGTH: 37
<212> TYPE: DNA
<213> ORGANISM: Artificial Sequence
<220> FEATURE:
```

<223> OTHER INFORMATION: primer

<400> SEQUENCE: 15
cggggtacca ctagtggttt tctgggggta tttgctg                                    37

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cgagtttctc cgtatctaat                                                       20

<210> SEQ ID NO 17
<211> LENGTH: 19
<212> TYPE: DNA
<213> ORGANISM: Artificial Sequence
<220> FEATURE:
<223> OTHER INFORMATION: primer

<400> SEQUENCE: 17
tcctcatcta taccccagg                                                        19

<210> SEQ ID NO 18
<211> LENGTH: 957
<212> TYPE: DNA
<213> ORGANISM: Artificial Sequence
<220> FEATURE:
<223> OTHER INFORMATION: XM_002491428.1

<400> SEQUENCE: 18
atgaatagcg tcatcactca agttgaagag aacaggtctg atagccatct gtccagtgaa           60
gcacagcagt ttgacgatga ctataacact gagatccggc tcaacatacg cggaactagc          120
gcaaccatta ccagagatga actgatggca ctaccagaaa gcattctact gtgtttgttt          180
cccaacggag tgtttgtaga tatcgaagga aatgtcatca caaaccttac agaggaggat          240
gttgtgtacg taaatttctc accagagtgc ttcaactata tagtggatac tttcaacgaa          300
gcagcagcct ccgatatcaa tagagtccac gacgaaaggc tagtgatcga agatggtgcc          360
gacctgttgc agagcaagcc ttcagttatc gttcttcgtg aggatctcga ctactattgt          420
atcccgcccg tccaaggaat gagcaaagaa cagatgattc aagtcaaaat agaagttgga          480
cattcactag tcaatgaggc acacatattt aagggtcttg ccatcaaca gaataagact           540
ttgggtcctg ctgagcagca ccttgcggat atgctgtgct catcgggatt cgttgctgac          600
ggttgctggg ccaccggtc tttagaacct gataagacag ttgtgttctc cctagcattg           660
gtgcgattga agccagacag ccctgaagat actaccaaca ccaagaaatc taaattcaac          720
acattgcaat accgtaactc ccgaaaaaag gccaaagaaa acactacagc cacaaaactt          780
ctgctatttt ggaggaagcc agctcgtaaa tgttggtggg ccagtgaaat gatcaaaacc          840
gatctctcaa gacttaattt gaaagacagc aatggaaatc ccatttcaac ggtggaaatt          900
aaagttcaca ttagaagagt ttggactttg gagttgtcag tgattggagt gcaataa             957

<210> SEQ ID NO 19
<211> LENGTH: 1710
<212> TYPE: DNA
<213> ORGANISM: Artificial Sequence
<220> FEATURE:
<223> OTHER INFORMATION: XM_002490375.1

<400> SEQUENCE: 19

```
atgttttcta gaagcgctag gcaattgggt agtgggagca tattgaggag tccacttcgt    60
tctgcgttcc gtcgggctgc ttctaccacc ccaactactc cagtcccacc accacccccct   120
ccaattccag ctactactcc agtggttaag aagaagagaa tcggcttttt ccgtttgact   180
tggagactga cctggctatc gttgttgggt agtgctgcgt acttgactta cgaggtttac   240
aaggaagtca atccttctcc acagatccca caaagtcctc tgaagccaaa tggaaaccgt   300
cggaaaaccg tcgtcatctt gggttccggt tggggtgcaa tttccacttt gaaacatttg   360
gatacttccc tgtacaacgt ggtcgtcgtc tctccaagaa actactttt gttcacccca   420
ttgcttcctt ccgttccgac cggaactatc gacttgaaat cgattataga ccctgtgaga   480
actatcgcca agtcaacccc aggtgaggtg acatatttgg aagctgaggc tactgatatc   540
gatattgcta agaaacaact gactatccaa cattcgtctt actctgccac ttctggtgtt   600
caccacgtca ctattggcgg agatgaagcc aagcctattg tcgcaactat tgaatatgac   660
tatctggtct tcgccattgg tgcacaaact gcaaccttcg gaattccagg aattgagaag   720
tatgcctact acctgaagga aactgatgat gctgccagaa tccgtcgttc tctgtttgaa   780
accattgaag cctctcaatt gcttccaaag gactccgaag agagaaaacg tttgttgtct   840
gtcgtcgtct gtggtggagg cccaactggc gttgagttgg ctgccgagat caaggactac   900
attgatgaag acctttccag atttgtgcca ggaattgaga acgaaatgtc cgttactcta   960
gtcgaagccc ttccaaatgt tctgaacgct tttaaccaca agttaattga gtacactgag  1020
tctatttttg agaagcagca attggacctt agagttaaca ccatggtcaa aaaggttgat  1080
gacaagaacg tttacgctac agtcaagaaa tctggtggtg acactgaaaa tgttacaatt  1140
ccatatggaa ctttagtttg ggccaccggt aatggtcctc gtcctttgac gaaagctgtt  1200
gctgcccaaa ttgaagagca gaaaactgca agaagaggcc tgcttatcgg cgaacatttg  1260
ttagtcgatg gcactgactc cgtgtttgcc cttggagatt gtaccttcac gaagaaccca  1320
cctaccgccc aagttgctca ccaagagggt atttatttag catctcattt ggccaaactc  1380
tccaagattg acgacctcaa gtatgaaatt ggtcagaaca ccgatcctga gcaattagtc  1440
cgcttgcagc gccgtttgga cagaacccaa gcttcgattc tgcctttcaa gtacactcac  1500
caaggtgctc tcgcatacat tggttccgaa cgtgctgttg ccgatttagt ttggggtgac  1560
tggtccaacg tttccactgg aggatcgctt acgttcctgt tctggagatc cgcctatgta  1620
tccatgatgt tgggagttcg taccaagatt tggtcgtctc tgattggat caaggtcaaa  1680
gtctttggaa gagattgttc caaggaataa                                    1710
```

<210> SEQ ID NO 20
<211> LENGTH: 1233
<212> TYPE: DNA
<213> ORGANISM: Artificial Sequence
<220> FEATURE:
<223> OTHER INFORMATION: XM_002493288.1

<400> SEQUENCE: 20

```
atgatatttg acggtactac gatgtcaatt gccattggtt tgctctctac tctaggtatt    60
ggtgctgaag ccaaagttca ttctgctaag atacacaagc atccagtctc agaaacttta   120
aaagaggcca attttgggca gtatgtctct gctctggaac ataaatatgt ttctctgttc   180
aacgaacaaa atgctttgtc caagtcgaat tttatgtctc agcaagatgg ttttgccgtt   240
```

```
gaagcttcgc atgatgctcc acttacaaac tatcttaacg ctcagtattt tactgaggta    300
tcattaggta cccctccaca atcgttcaag gtgattcttg acacaggatc ctccaattta    360
tgggttccta gcaaagattg tggatcatta gcttgcttct tgcatgctaa gtatgaccat    420
gatgagtctt ctacttataa gaagaatggt agtagctttg aaattaggta tggatccggt    480
tccatggaag ggtatgtttc tcaggatgtg ttgcaaattg gggatttgac cattcccaaa    540
gttgattttg ctgaggccac atcggagccg gggttggcct tcgcttttgg caaatttgac    600
ggaattttgg ggcttgctta tgattcaata tcagtaaata agattgttcc tccaatttac    660
aaggctttgg aattagatct ccttgacgaa ccaaaatttg ccttctactt gggggatacg    720
gacaaagatg aatccgatgg cggtttggcc acatttggtg gtgtggacaa atctaagtat    780
gaaggaaaga tcacctggtt gcctgtcaga agaaaggctt actgggaggt ctcttttgat    840
ggtgtaggtt tgggatccga atatgctgaa ttgcaaaaaa ctggtgcagc catcgacact    900
ggaacctcat tgattgcttt gcccagtggc ctagctgaaa ttctcaatgc agaaattggt    960
gctaccaagg gttggtctgg tcaatacgct gtggactgtg acactagaga ctcttttgcca   1020 gacttaactt taaccttcgc cggttacaac tttaccatta ctccatatga ctatactttg   1080
gaggtttctg ggtcatgtat tagtgctttc accccccatgg actttcctga accaataggt   1140
cctttggcaa tcattggtga ctcgttcttg agaaaatatt actcagttta tgacctaggc   1200
aaagatgcag taggtttagc caagtctatt tag                                 1233

<210> SEQ ID NO 21
<211> LENGTH: 351
<212> TYPE: PRT
<213> ORGANISM: Artificial Sequence
<220> FEATURE:
<223> OTHER INFORMATION: BQ9382_C1-2260, EKK deletion at positions
      308-310, a hypothetical protein

<400> SEQUENCE: 21

Met Pro Pro Lys Thr Pro Ala Trp Lys Lys Ile Gly Leu Lys Val Gln
1               5                   10                  15

Asn Glu Ile Leu Asn Asp Pro Phe Ser Val Glu His Leu Glu Gly Ala
                20                  25                  30

Ile Lys Thr Thr Lys Lys Arg Thr Arg Glu Pro Val Lys Ser Glu Pro
            35                  40                  45

Glu Gly Ser Lys Lys Ala Pro Lys Arg Lys Lys Leu Pro Lys Ser Glu
        50                  55                  60

Arg Pro Pro Pro Glu Lys Asp Gln Leu Ala Tyr Leu Arg Gln Phe
65                  70                  75                  80

His Glu Asp Arg Asp Asn Trp Lys Phe Ser Lys Gln Lys Gln Asn Trp
                85                  90                  95

Val Leu Arg His Leu Ser Val Ile Pro Ser Glu Tyr Glu Ala Ala Leu
                100                 105                 110

Ser Ser Tyr Leu Glu Gly Met Gln Gly Gln Ser Arg Asp Arg Leu Val
            115                 120                 125

Gly Glu Phe Lys Thr Val Val Glu Arg Trp Asn Ala Phe Cys Glu Gln
        130                 135                 140

Ala Glu Gln Lys Leu Ile Lys Gln Leu Glu Glu Asn Val Lys Asn Gly
145                 150                 155                 160

Gln Thr Lys Glu Glu Ala Glu Glu Lys Glu Gly Glu Asp Glu Glu Lys
                165                 170                 175
```

```
Glu Thr Lys Glu Glu Ile Lys Ala Pro Glu Tyr Asp Tyr Val Ile Arg
                180                 185                 190

Ala Ser Arg Leu Phe Asn Val Leu Thr Gly Glu Lys Ile Tyr Val Lys
            195                 200                 205

Asn Val Glu Met Glu Glu Lys Glu Glu Lys Glu Gly Glu Glu
210                 215                 220

Lys Asp Leu Val Glu Glu Lys Gln Glu Asn Asp Glu Lys Val Glu
225                 230                 235                 240

Glu Ile Asp His Lys His Lys Ser Lys Asp Arg Glu Asp Ala Glu Asp
                245                 250                 255

Val Arg Asp Glu Gly Leu Ser Asn Leu Ile Val Glu Lys Val Glu Val
                260                 265                 270

Thr Glu Phe Ile Asp Asp Thr Asp Tyr Leu Asp Lys Asp Glu Lys Asp
            275                 280                 285

Ala Glu Glu Ser Glu Ala Thr Asn Gly Asp Lys Gln Asp Glu Thr
290                 295                 300

Glu Lys Lys Glu Lys Glu Lys Lys Glu Lys Lys Glu Lys Lys Glu
305                 310                 315                 320

Lys Glu Lys Lys Glu Lys Lys Glu Lys Lys Glu Lys Lys Glu Lys Lys
                325                 330                 335

Glu Lys Lys Glu Lys Lys Lys Glu Lys Lys Glu Arg Lys Ser Thr
                340                 345                 350

<210> SEQ ID NO 22
<211> LENGTH: 212
<212> TYPE: PRT
<213> ORGANISM: Artificial Sequence
<220> FEATURE:
<223> OTHER INFORMATION: BQ9382_C1-3800, E129K, 60S ribosomal subunit
      assembly/export protein LOC1

<400> SEQUENCE: 22

Met Pro Arg Asn Lys Thr Gln Ala Ala Lys Lys Lys Asn Pro Glu Asn
1               5                   10                  15

Phe Arg Arg Ser Val Glu Ser Asp Val Phe Thr Asp Ser Glu Ala Arg
                20                  25                  30

Asn Arg Leu Ala Ser Gln Pro Lys Lys Thr Ala Lys Ser Lys Val His
            35                  40                  45

Lys Gln Ser His Leu Glu Val Lys Lys Glu Gln Arg Ser Val Arg Leu
        50                  55                  60

Tyr Gly Lys Lys Pro Leu Arg Glu Tyr Thr Glu Lys Glu Leu His
65                  70                  75                  80

Ile Pro Val Leu Asn Arg Ala Ile Val Pro Gly Val Val Pro Lys Ala
                85                  90                  95

Arg Gly Lys Lys Gly Lys Lys Phe Val Asp Asp His Asp Ser Val Val
                100                 105                 110

Leu Thr Arg Leu Val Lys Gln Ile Asn Asp Lys Lys Asp Leu Leu Asn
            115                 120                 125

Lys Ser Lys Leu Glu Lys Ser Gln Arg Ile Glu Glu Ile Arg Glu Leu
        130                 135                 140

Lys Lys Gln Glu Ile Glu Lys Lys Glu Glu Leu Lys Lys Gln Lys Leu
145                 150                 155                 160

Asp Asp Lys Lys Gln Gln Ile Lys Ser Lys Ala Asn Thr Ala Arg Ala
                165                 170                 175
```

-continued

```
Ile Arg Arg Arg Asn Ala Arg Glu Leu Ala Arg Lys Ala Lys Glu Asn
            180                 185                 190

Ala Asp Glu Lys Leu Thr Thr Arg Asn Ile Lys Lys Pro Ile Lys Ser
        195                 200                 205

Val Ser Phe Ala
    210

<210> SEQ ID NO 23
<211> LENGTH: 569
<212> TYPE: PRT
<213> ORGANISM: Artificial Sequence
<220> FEATURE:
<223> OTHER INFORMATION: BQ9382_C1-5700, I312M, mitochondrial external
      NADH dehydrogenase, class II NAD(P)H:quinone oxidoreductase

<400> SEQUENCE: 23

Met Phe Ser Arg Ser Ala Arg Gln Leu Gly Ser Gly Ser Ile Leu Arg
1               5                   10                  15

Ser Pro Leu Arg Ser Ala Phe Arg Arg Ala Ala Ser Thr Thr Pro Thr
            20                  25                  30

Thr Pro Val Pro Pro Pro Pro Pro Ile Pro Ala Thr Thr Pro Val
        35                  40                  45

Val Lys Lys Lys Arg Ile Gly Phe Phe Arg Leu Thr Trp Arg Leu Thr
    50                  55                  60

Trp Leu Ser Leu Leu Gly Ser Ala Ala Tyr Leu Thr Tyr Glu Val Tyr
65                  70                  75                  80

Lys Glu Val Asn Pro Ser Pro Gln Ile Pro Gln Ser Pro Leu Lys Pro
                85                  90                  95

Asn Gly Asn Arg Arg Lys Thr Val Val Ile Leu Gly Ser Gly Trp Gly
            100                 105                 110

Ala Ile Ser Thr Leu Lys His Leu Asp Thr Ser Leu Tyr Asn Val Val
        115                 120                 125

Val Val Ser Pro Arg Asn Tyr Phe Leu Phe Thr Pro Leu Leu Pro Ser
    130                 135                 140

Val Pro Thr Gly Thr Ile Asp Leu Lys Ser Ile Ile Asp Pro Val Arg
145                 150                 155                 160

Thr Ile Ala Lys Ser Thr Pro Gly Glu Val Thr Tyr Leu Glu Ala Glu
                165                 170                 175

Ala Thr Asp Ile Asp Ile Ala Lys Lys Gln Leu Thr Ile Gln His Ser
            180                 185                 190

Ser Tyr Ser Ala Thr Ser Gly Val His His Val Thr Ile Gly Gly Asp
        195                 200                 205

Glu Ala Lys Pro Ile Val Ala Thr Ile Glu Tyr Asp Tyr Leu Val Phe
    210                 215                 220

Ala Ile Gly Ala Gln Thr Ala Thr Phe Gly Ile Pro Gly Ile Glu Lys
225                 230                 235                 240

Tyr Ala Tyr Tyr Leu Lys Glu Thr Asp Asp Ala Ala Arg Ile Arg Arg
                245                 250                 255

Ser Leu Phe Glu Thr Ile Glu Ala Ser Gln Leu Leu Pro Lys Asp Ser
            260                 265                 270

Glu Glu Arg Lys Arg Leu Leu Ser Val Val Val Cys Gly Gly Gly Pro
        275                 280                 285

Thr Gly Val Glu Leu Ala Ala Glu Ile Lys Asp Tyr Ile Asp Glu Asp
    290                 295                 300
```

```
Leu Ser Arg Phe Val Pro Gly Met Glu Asn Glu Met Ser Val Thr Leu
305                 310                 315                 320

Val Glu Ala Leu Pro Asn Val Leu Asn Ala Phe Asn His Lys Leu Ile
            325                 330                 335

Glu Tyr Thr Glu Ser Ile Phe Glu Lys Gln Gln Leu Asp Leu Arg Val
        340                 345                 350

Asn Thr Met Val Lys Val Asp Asp Lys Asn Val Tyr Ala Thr Val
    355                 360                 365

Lys Lys Ser Gly Gly Asp Thr Glu Asn Val Thr Ile Pro Tyr Gly Thr
370                 375                 380

Leu Val Trp Ala Thr Gly Asn Gly Pro Arg Pro Leu Lys Ala Val
385                 390                 395                 400

Ala Ala Gln Ile Glu Glu Gln Lys Thr Ala Arg Arg Gly Leu Leu Ile
                405                 410                 415

Gly Glu His Leu Leu Val Asp Gly Thr Asp Ser Val Phe Ala Leu Gly
            420                 425                 430

Asp Cys Thr Phe Thr Lys Asn Pro Pro Thr Ala Gln Val Ala His Gln
        435                 440                 445

Glu Gly Ile Tyr Leu Ala Ser His Leu Ala Lys Leu Ser Lys Ile Asp
    450                 455                 460

Asp Leu Lys Tyr Glu Ile Gly Gln Asn Thr Asp Pro Glu Gln Leu Val
465                 470                 475                 480

Arg Leu Gln Arg Arg Leu Asp Arg Thr Gln Ala Ser Ile Leu Pro Phe
                485                 490                 495

Lys Tyr Thr His Gln Gly Ala Leu Ala Tyr Ile Gly Ser Glu Arg Ala
            500                 505                 510

Val Ala Asp Leu Val Trp Gly Asp Trp Ser Asn Val Ser Thr Gly Gly
        515                 520                 525

Ser Leu Thr Phe Leu Phe Trp Arg Ser Ala Tyr Val Ser Met Met Leu
    530                 535                 540

Gly Val Arg Thr Lys Ile Leu Val Val Ser Asp Trp Ile Lys Val Lys
545                 550                 555                 560

Val Phe Gly Arg Asp Cys Ser Lys Glu
                565
```

<210> SEQ ID NO 24
<211> LENGTH: 144
<212> TYPE: PRT
<213> ORGANISM: Artificial Sequence
<220> FEATURE:
<223> OTHER INFORMATION: BQ9382_C2-3950, Q145X, an essential protein having a binding partner Psr1p and used for completely activating a general stress response

<400> SEQUENCE: 24

```
Met Asn Ser Val Ile Thr Gln Val Glu Glu Asn Arg Ser Asp Ser His
1               5                   10                  15

Leu Ser Ser Glu Ala Gln Gln Phe Asp Asp Tyr Asn Thr Glu Ile
            20                  25                  30

Arg Leu Asn Ile Arg Gly Thr Ser Ala Thr Ile Thr Arg Asp Glu Leu
        35                  40                  45

Met Ala Leu Pro Glu Ser Ile Leu Leu Cys Leu Phe Pro Asn Gly Val
    50                  55                  60

Phe Val Asp Ile Glu Gly Asn Val Ile Thr Asn Leu Thr Glu Glu Asp
65                  70                  75                  80
```

```
Val Val Tyr Val Asn Phe Ser Pro Glu Cys Phe Asn Tyr Ile Val Asp
                85                  90                  95

Thr Phe Asn Glu Ala Ala Ala Ser Asp Ile Asn Arg Val His Asp Glu
            100                 105                 110

Arg Leu Val Ile Glu Asp Gly Ala Asp Leu Leu Gln Ser Lys Pro Ser
        115                 120                 125

Val Ile Val Leu Arg Glu Asp Leu Asp Tyr Tyr Cys Ile Pro Pro Val
130                 135                 140

<210> SEQ ID NO 25
<211> LENGTH: 212
<212> TYPE: PRT
<213> ORGANISM: Artificial Sequence
<220> FEATURE:
<223> OTHER INFORMATION: BQ9382_C3-2220, E188K, a hypothetical protein

<400> SEQUENCE: 25

Met Ala Pro His Pro Ser Ser Ile Leu Phe Gly Val Gln Glu Gly Tyr
1               5                   10                  15

Gln Leu Thr Ala Val Ser Leu Lys Ser Asn Ile Ala Thr Lys Tyr Val
            20                  25                  30

Leu Asn Asn Glu Leu Ile Ser Gly Leu Leu His Leu Thr Gln Glu Ser
        35                  40                  45

Phe Asn Gly Asp Thr Asn Val Asp Phe Thr Lys Ile Asn Pro Ser Leu
    50                  55                  60

Ala Thr Asp Pro Gln His Tyr Glu Glu Trp Ser Lys Ile Leu Gln Lys
65                  70                  75                  80

Gln Val Asp Ala Leu Glu Lys Glu Gln Asp Leu Pro Asp Ser Thr Tyr
                85                  90                  95

Gln Glu Leu Glu Ser Leu Asp Asn Asp Ile Ala Asn Leu Glu Arg Glu
            100                 105                 110

Tyr Leu Thr Arg Tyr Lys Leu Asp Ser Lys Leu Glu Glu Asp Lys Asp
        115                 120                 125

Lys Gln Pro Ile Arg Glu Leu Val Ala Leu Asn Asp Gln Ile Leu Thr
130                 135                 140

Arg Phe Gln Thr Lys Tyr His Lys Tyr Val Tyr Glu Val Thr Gly Asp
145                 150                 155                 160

Leu Asn Thr Val Pro His Val Thr Val Val Thr Asp Lys Gly Glu Val
                165                 170                 175

Gln Glu Ser Thr Gln Pro Glu Glu Asp Glu Asp Lys Asp Val Glu Asp
            180                 185                 190

Thr Thr Pro Gln Glu Tyr Pro Ser Asn Thr Tyr Tyr Arg Ile Gln Lys
        195                 200                 205

Arg Leu Val Phe
    210

<210> SEQ ID NO 26
<211> LENGTH: 195
<212> TYPE: PRT
<213> ORGANISM: Artificial Sequence
<220> FEATURE:
<223> OTHER INFORMATION: BQ9382_C3-4370, W196X, orotidine 5\'-phosphate
      decarboxylase

<400> SEQUENCE: 26

Met Ala Arg Ser Tyr Ala Glu Arg Ala Asn Thr His Gln Ser Pro Val
1               5                   10                  15
```

Ala Arg Arg Leu Phe Ala Leu Met Glu Gln Lys Gln Ser Asn Leu Cys
            20                  25                  30

Ala Ser Val Asp Val Arg Thr Thr Lys Glu Leu Leu Glu Leu Leu Asp
         35                  40                  45

Lys Leu Gly Pro Phe Ile Cys Leu Ala Lys Thr His Ile Asp Ile Ile
 50                  55                  60

Asp Asp Phe Thr Tyr Asp Gly Thr Ile Leu Pro Leu Leu Glu Leu Ser
 65                  70                  75                  80

Lys Lys His Lys Phe Leu Ile Phe Glu Asp Arg Lys Phe Ala Asp Ile
                 85                  90                  95

Gly Asn Thr Val Lys His Gln Tyr Gln Gly Gly Val Tyr Lys Ile Ala
            100                 105                 110

Gln Trp Ala Asp Ile Thr Asn Ala His Gly Val Ile Gly Ser Gly Ile
        115                 120                 125

Val Lys Gly Leu Lys Glu Ala Ala Thr Glu Thr Thr Asp Gln Pro Arg
130                 135                 140

Gly Leu Leu Met Leu Ala Glu Leu Ser Ser Lys Gly Ser Ile Ala His
145                 150                 155                 160

Gly Lys Tyr Thr Glu Glu Thr Val Glu Ile Ala Lys Ser Asp Lys Glu
                165                 170                 175

Phe Val Ile Gly Phe Ile Ala Gln Asn Ser Met Gly Gly Gln Asp Glu
            180                 185                 190

Gly Phe Asp
       195

<210> SEQ ID NO 27
<211> LENGTH: 1047
<212> TYPE: DNA
<213> ORGANISM: Artificial Sequence
<220> FEATURE:
<223> OTHER INFORMATION: BQ9382_C1-2260, EKK deletion at positions
      308-310, a hypothetical protein

<400> SEQUENCE: 27
atgcccccaa agaccccagc gtggaagaaa attggcctca aggtccaaaa tgagattttg      60
aatgacccct ttagtgtgga acatttagaa ggagctataa aaaccacaaa gaaacgcaca     120
cgagagcctg tcaaaagtga gcctgagggg agtaagaagg ctccaaagag aaagaagtta     180
cccaaatcag aaaggccacc cccaccagaa aaagatcagc ttgcttatct tagacagttt     240
catgaggata gagataattg gaaattttcc aagcagaaac agaactgggt gttgagacac     300
ctttctgtta ttccttccga gtatgaggca gctctaagta gttacctgga gggaatgcag     360
gggcaatctc gagaccgttt ggttggagag ttcaaaacgg ttgtagaacg atggaatgcg     420
ttctgtgagc aagcagagca gaagctgata aagcaacttg aggaaaacgt aaagaacgga     480
cagaccaagg aagaggcaga ggaaaaggaa ggagaagatg aagagaagga gacaaaggaa     540
gagatcaagg ctcctgagta tgattatgtg atcagagcca gcagattgtt taatgttctt     600
actggagaga agatatacgt gaaaaacgtc gaaatggagg aagagaagga ggaagagaag     660
gaggggaaag aaaagagatt tagtagaggaa gaaaaacagg aaaatgatga aaagtagag      720 gaaatagatc ataaacataa atcaaaagac agggaagatg cagaggatgt tagggatgaa     780
ggtttgagca atttaattgt ggagaaggtc gaagtaaccg agtttattga cgatactgac     840
tatttggaca agatgaaaaa ggacgcagag gaatccgagg ctactaatga agataagcag     900
gatgaggaaa ccgaaaagaa ggagaagaag gagaagaaag aaagaaagga gaagaaagaa     960

```
aagaaggaga aggagaagaa ggagaagaag gagaagaagg agaagaagga gaagaagaaa    1020
gaaaagaaag aacgaaaatc tacctga                                       1047

<210> SEQ ID NO 28
<211> LENGTH: 639
<212> TYPE: DNA
<213> ORGANISM: Artificial Sequence
<220> FEATURE:
<223> OTHER INFORMATION: BQ9382_C1-3800, E129K, 60S ribosomal subunit
      assembly/export protein LOC1

<400> SEQUENCE: 28
atgcctcgca ataagactca agctgctaaa aagaagaatc cggaaaattt tagaagatct     60
gttgaatcag atgtctttac tgactccgaa gctcgtaatc ggctagcgtc tcaaccaaaa    120
aaaactgcga atcaaaggt tcacaaacag agtcacttgg aagttaagaa agaacaaaga    180
tcggtacggt tgtatggaaa aaaaaaacca cttagagaat ataccgaaaa agaacttcat    240
attcctgtat taaacagagc catagttcct ggtgttgttc cgaaagctcg aggtaaaaag    300
ggaaagaagt ttgtggacga tcacgattct gtcgttttaa ccagacttgt caaacaaatc    360
aacgacaaaa aggacttgct gaacaagagt aaattagaga aatcacaacg tattgaagag    420
atccgtgagt taaagaaaca agaaattgaa aaaaagagg agcttaagaa gcaaaaattg    480
gacgataaga acaacagat taaatcgaag gccaatactg caagagctat tcgaagaagg    540
aacgccagag agcttgccag aaaggcgaag gaaaacgctg atgaaaaact aactactcgg    600
aacattaaaa aacctatcaa atctgtgtca tttgcttaa                          639

<210> SEQ ID NO 29
<211> LENGTH: 1710
<212> TYPE: DNA
<213> ORGANISM: Artificial Sequence
<220> FEATURE:
<223> OTHER INFORMATION: BQ9382_C1-5700, I312M, mitochondrial external
      NADH dehydrogenase, class II NAD(P)H:quinone oxidoreductase

<400> SEQUENCE: 29
atgttttcta gaagcgctag gcaattgggt agtgggagca tattgaggag tccacttcgt     60
tctgcgttcc gtcgggctgc ttctaccacc ccaactactc cagtcccacc accacccct    120 ccaattccag ctactactcc agtggttaag aagaagagaa tcggctttt ccgtttgact    180 tggagactga cctggctatc gttgttgggt agtgctgcgt acttgactta cgaggtttac    240
aaggaagtca atccttctcc acagatccca caaagtcctc tgaagccaaa tggaaaccgt    300
cggaaaaccg tcgtcatctt gggttccggt tggggtgcaa tttccacttt gaaacatttg    360
gatacttccc tgtacaacgt ggtcgtcgtc tctccaagaa actacttttt gttcacccca    420
ttgcttcctt ccgttccgac cggaactatc gacttgaaat cgattataga ccctgtgaga    480
actatcgcca agtcaacccc aggtgaggtg acatatttgg aagctgaggc tactgatatc    540
gatattgcta agaaacaact gactatccaa cattcgtctt actctgccac ttctggtgtt    600
caccacgtca ctattggcgg agatgaagcc aagcctattg tcgcaactat tgaatatgac    660
tatctggtct tcgccattgg tgcacaaact gcaaccttcg gaattccagg aattgagaag    720
tatgcctact acctgaagga aactgatgat gctgccagaa tccgtcgttc tctgtttgaa    780
accattgaag cctctcaatt gcttccaaag gactccgaag agagaaaacg tttgttgtct    840
gtcgtcgtct gtggtggagg cccaactggc gttgagttgg ctgccgagat caaggactac    900
```

```
attgatgaag accttttccag atttgtgcca ggaatggaga acgaaatgtc cgttactcta    960
gtcgaagccc ttccaaatgt tctgaacgct tttaaccaca agttaattga gtacactgag   1020
tctatttttg agaagcagca attggacctt agagttaaca ccatggtcaa aaaggttgat   1080
gacaagaacg tttacgctac agtcaagaaa tctggtggtg acactgaaaa tgttacaatt   1140
ccatatggaa ctttagtttg ggccaccggt aatggtcctc gtcctttgac gaaagctgtt   1200
gctgcccaaa ttgaagagca gaaaactgca agaagaggcc tgcttatcgg cgaacatttg   1260
ttagtcgatg gcactgactc cgtgtttgcc cttggagatt gtaccttcac gaagaaccca   1320
cctaccgccc aagttgctca ccaagagggt atttatttag catctcattt ggccaaactc   1380
tccaagattg acgacctcaa gtatgaaatt ggtcagaaca ccgatcctga gcaattagtc   1440
cgcttgcagc gccgtttgga cagaacccaa gcttcgattc tgcctttcaa gtacactcac   1500
caaggtgctc tcgcatacat tggttccgaa cgtgctgttg ccgatttagt ttgggggtgac  1560
tggtccaacg tttccactgg aggatcgctt acgttcctgt tctggagatc cgcctatgta   1620
tccatgatgt tgggagttcg taccaagatt ttggtcgtct ctgattggat caaggtcaaa   1680
gtctttggaa gagattgttc caaggaataa                                     1710

<210> SEQ ID NO 30
<211> LENGTH: 435
<212> TYPE: DNA
<213> ORGANISM: Artificial Sequence
<220> FEATURE:
<223> OTHER INFORMATION: BQ9382_C2-3950, Q145X, an essential protein
      having a binding partner Psr1p and used for completely activating
      a general stress response

<400> SEQUENCE: 30
atgaatagcg tcatcactca agttgaagag aacaggtctg atagccatct gtccagtgaa     60
gcacagcagt ttgacgatga ctataacact gagatccggc tcaacatacg cggaactagc    120
gcaaccatta ccagagatga actgatggca ctaccagaaa gcattctact gtgtttgttt    180
cccaacggag tgtttgtaga tatcgaagga aatgtcatca caaaccttac agaggaggat    240
gttgtgtacg taaatttctc accagagtgc ttcaactata tagtggatac tttcaacgaa    300
gcagcagcct ccgatatcaa tagagtccac gacgaaaggc tagtgatcga agatggtgcc    360
gacctgttgc agagcaagcc ttcagttatc gttcttcgtg aggatctcga ctactattgt    420
atcccgcccg tctaa                                                     435

<210> SEQ ID NO 31
<211> LENGTH: 639
<212> TYPE: DNA
<213> ORGANISM: Artificial Sequence
<220> FEATURE:
<223> OTHER INFORMATION: BQ9382_C3-2220, E188K, a hypothetical protein

<400> SEQUENCE: 31
atggctcctc atccgtcatc gatcttgttt ggggtccaag agggctatca gctgacagca     60
gtgtctctca aatcaaacat agcaaccaaa tatgtgctta ataatgagtt aatttccggt    120
ttattgcatc tcacgcagga atctttcaac ggggacacca acgttgactt taccaagatc    180
aatccttccc tggcaacgga tccccaacat tatgaagaat ggagcaaaat attacagaag    240
caagttgatg cactggagaa ggaacaagac ctaccagatt ccacctacca agagcttgaa    300
tctctctgaca atgacattgc caatctgaaa agggaatatc tcacgagata caacttgat    360
tctaaacttg aggaggacaa agataaacaa cctattcggg aactggtcgc actcaacgat    420
```

```
cagatactga caagattcca aaccaaatat cacaagtacg tctacgaagt cacgggagac    480
ttgaataccg taccgcatgt cacggtcgtc acagacaaag gcgaagttca ggaatcaaca    540
cagccagagg aggacgagga tgaagatgta gaagacacaa cgccccaaga gtatccaagc    600
aacacatact accggattca aaaacgctta gttttctag                          639

<210> SEQ ID NO 32
<211> LENGTH: 588
<212> TYPE: DNA
<213> ORGANISM: Artificial Sequence
<220> FEATURE:
<223> OTHER INFORMATION: BQ9382_C3-4370, W196X, orotidine 5\'-phosphate
      decarboxylase

<400> SEQUENCE: 32
atggctcgca gttatgccga gagagcaaat actcatcaat cacctgtggc acgacgactg     60
tttgcgctta tggaacagaa acagagtaac ctatgcgcat cagtcgacgt gagaacaact   120
aaagaattat tggagcttct agataaattg ggcccattta tctgtttggc caagactcat   180
atcgacataa ttgatgactt cacgtatgat ggaactattc tgcctttatt ggaactatca   240
aagaaacaca agtttttaat ttttgaggac agaaagtttg ctgatatagg caacactgtc   300
aagcatcaat atcaaggagg tgtctacaag attgcacaat gggcagatat tacaaatgct   360
catggtgtca ttggtagtgg aattgtaaag ggtctaaagg aggcagccac tgagacaaca   420
gatcaaccaa ggggactatt gatgttggct gaactgtcgt caaagggatc aattgcccat   480
ggtaagtaca ccgaagaaac tgtagaaatt gcaaaatcag acaaggaatt cgtcattggg   540
tttattgctc aaaattctat gggaggacaa gatgaagggt tcgattga                588
```

PICHIA PASTORIS MUTANT STRAIN FOR EXPRESSING EXOGENOUS GENE

CROSS-REFERENCE TO RELATED APPLICATIONS

This application is a 35 U.S.C. § 371 national stage filing of International Application No. PCT/CN2019/129359, filed on Dec. 27, 2019, which in turn claims the benefit of Chinese Patent Application No. 201811619556.3, filed on Dec. 28, 2018. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Oct. 30, 2024, is named 127001-00502_SL.txt and is 46,030 bytes in size.

TECHNICAL FIELD

The present invention relates to *Pichia* mutant strains for expressing exogenous genes.

BACKGROUND TECHNIQUE

The *Pichia pastoris* expression system is a new type of exogenous protein expression system developed in the early 1980s. It has the advantages of easy operation, easy culture, fast growth, high expression, and low cost, etc. of prokaryotic expression system, and also has the characteristics of post-translational modification of exogenous proteins etc. which prokaryotic expression system does not have, such as glycosylation, protein phosphorylation, etc. At the same time, it also avoids the defects of *Saccharomyces cerevisiae*, such as the secretion efficiency is poor, the expression strain is not stable enough, and the expression plasmid is easy to lose. Therefore, this expression system has quickly become one of the best and most widely used exogenous gene expression systems now.

Koichi Ogata et al. first discovered in 1969 that certain yeasts can use methanol as the sole carbon source and energy source for growth (Ogata, et al. 1969). Since then, the potential of using methanol-utilizing yeast to produce single-cell protein as animal feed has received widespread attention. In 1987, Cregg et al. reported the use of methanol-trophic yeast to express hepatitis B surface antigen (HbsAg) for the first time, and then Philip Petroleum and Salk Institute Biotechnology/Industrial Associates (SIBIA) began the cooperative development of the *Pichia* expression system. Researchers of SIBIA isolated the promoter and host strain of the AOX gene, constructed the vector, and developed the corresponding *Pichia* gene manipulation technology. It was combined with the fermentation process for producing single-cell protein of Philip Petroleum, and achieved the efficient expression of exogenous proteins. In 1993, Philip Petroleum sold the patent of the *Pichia* expression system to Research Corporation Technologies (RCT).

RCT's basic strain GS115 is derived from chemically mutagenizing the original strain NRRL-Y 11430 (ATCC 76273), and making it a histidine auxotrophic host (His-), which is convenient for clone screening. The alcohol oxidase gene AOX1 of GS115 is complete, and it has been able to use methanol to express most exogenous proteins, but its background AOX1 is still efficiently expressed. So the yield of some genes is affected. One of the subsequent direction of *Pichia*-derived strains was to knock out the AOX1 gene on the basis of GS115 and replace it with the *Saccharomyces cerevisiae* ARG4 gene to obtain KM71 (his4 arg4 aox1Δ::ARG4), whose AOX2 gene remained intact, and thus had low methanol utilization rate and grew very slowly under the cultivation with methanol as the sole carbon source. The AOX2 gene was further knocked out, and the host MC100-3 (his4 arg4 aox1Δ::SARG4aox2Δ::Phis4) that could not use methanol was obtained. Another direction modified on the basis of GS115 was to inactivate the host protease. *Pichia* vacuolar protease B (Proteinase B, prb1) was knocked out to obtain SMD1165 (his4 prb1), or vacuolar aspartic protease (PEP4) was knocked out to obtain SMD1168 (his4 pep4). This protease was used to activate other vacuolar proteases, including carboxypeptidase Y and protease B. Then, on the basis of SMD1168, vacuolar protease B (Proteinase B, prb1) was further knocked out to obtain SMD1163 (his4 pep4 prb1). That is, PEP4 protease is more critical and is used for the activation of some proteases. If necessary, the vacuolar protease prb1 and carboxypeptidase can be further knocked out.

SUMMARY OF THE INVENTION

The present invention engineered *Pichia* CICC32806 to obtain a *Pichia* which can be used to efficiently express various proteins, especially phospholipases and lipases.

The first aspect of the present invention is to provide a *Pichia* strain, which comprises one or more of the following 6 mutations compared with *Pichia* strain GS115 or CICC32806: genes encoding BQ9382_C1-2260, EKK deletion at positions 308-310, a hypothetical protein (SEQ ID NO:21); BQ9382_C1-3800, E129K, 60S ribosomal subunit assembly/export protein LOC1 (SEQ ID NO:22); BQ9382_C1-5700, 1312M, mitochondrial external NADH dehydrogenase, class II NAD(P)H: quinone oxidoreductase (SEQ ID NO: 23); BQ9382_C2-3950, Q145X, an essential protein having a binding partner Psr1p and used for completely activating a general stress response (SEQ ID NO:24); BQ9382_C3-2220, E188K, a hypothetical protein (SEQ ID NO: 25); and BQ9382_C3-4370, W196X, orotidine 5\'-phosphate decarboxylase (SEQ ID NO:26).

In one or more embodiments, the strain includes 6 mutations as described above.

The *Pichia* strains are a *Pichia pastoris* strain with a deposit number of CGMCC No. 16670, a *Pichia pastoris* strain with a deposit number of CGMCC No. 16669, and a *Pichia pastoris* strain with a deposit number of CGMCC No. 19221.

In one or more embodiments, the *Pichia* strain provided by the present invention is a histidine and uracil double-deficient strain.

In one or more embodiments, the present invention provides a *Pichia pastoris* strain with a deposit number of CGMCC No. 16670.

The present invention also provides a genetically engineered *Pichia* strain, which is a genetically engineered *Pichia pastoris* strain with a deposit number of CGMCC No. 16670, and (a) is a histidine deficient strain; and/or (b) comprises a plasmid expressing a growth promoting factor, and/or integrates an encoding sequence of a growth promoting factor in the genome, and/or expresses a growth promoting factor.

In one or more embodiments, the genetically engineered *Pichia* strain is a *Pichia pastoris* strain with a deposit number of CGMCC No. 16669.

The *Pichia* strain described in any of the foregoing embodiments can be used as a basic strain to be genetically engineered to express exogenous genes of interest. Therefore, the present invention also provides a genetically engineered *Pichia* strain, which is the *Pichia* strain according to any one of the foregoing embodiments that has been genetically engineered to comprise an exogenous gene or a vector comprising the exogenous gene, including the genetically engineered *Pichia pastoris* (*Pichia pastoris*) strain of CGMCC No. 16670 comprising the exogenous gene or a vector comprising the exogenous gene, the histidine and uracil double-deficient strain, the histidine single-deficient strain, and/or a genetically engineered *Pichia* strain which comprises a plasmid expressing a growth promoting factor, which integrates an encoding sequence of a growth promoting factor in the genome and/or which expresses a growth promoting factor, and the *Pichia pastoris* strain with a deposit number of CGMCC No. 16669. It should be understood that the exogenous gene described here does not include the gene encoding the growth promoting factor, and any other exogenous genes of interest can be included by genetic engineering in addition to the gene expressing the growth promoting factor.

In one or more embodiments, an exogenous gene is integrated in the genome of the strain.

In one or more embodiments, the exogenous gene is an encoding sequence of a protein used in the field of industry, feed or food.

In one or more embodiments, the exogenous gene is an encoding sequence of an enzyme. Preferably, the enzyme is at least one selected from the following enzymes: a lipase, a protease, a cellulase, an amylase, a phytase, an esterase, a pectinase, a galactosidase and a phospholipase.

The present invention also provides a culture comprising the *Pichia* strain according to any embodiment of the present invention and optionally, a culture medium.

In one or more embodiments, the medium is a seed medium or a fermentation medium.

In one or more embodiments, the medium is YPD medium or BMMY medium.

The present invention also provides an enzyme preparation, which comprises fermentation broth of the *Pichia* according to any embodiment of the present invention having an exogenous gene which is an encoding sequence of the enzyme, lysate of the cells obtained by fermentation, or concentrate of said fermentation broth or lysate.

The present invention also provides use of the enzyme preparation of the present invention in transesterification, wherein the enzyme preparation comprises fermentation broth of the *Pichia* according to any embodiment of the present invention having an exogenous gene which is an encoding sequence of a lipase, lysate of the cells obtained by fermentation, or concentrate of said fermentation broth or lysate.

The present invention also provides use of the enzyme preparation of the present invention in oil degumming, wherein the enzyme preparation comprises fermentation broth of the *Pichia* according to any embodiment of the present invention having an exogenous gene which is an encoding sequence of a phospholipase (preferably a phospholipase C), lysate of the cells obtained by fermentation, or concentrate of said fermentation broth or lysate.

In one or more embodiments, the amino acid sequence of the lipase is an amino acid sequence having at least 80%, 90%, 95%, 98%, or 99% identity with SEQ ID NO: 7 or 9. More preferably, the amino acid sequence of the lipase is shown in SEQ ID NO: 7 or 9.

In one or more embodiments, the amino acid sequence of the phospholipase is an amino acid sequence having at least 80%, 90%, 95%, 98%, or 99% identity with SEQ ID NO: 2. More preferably, the amino acid sequence of the phospholipase is shown in SEQ ID NO: 2.

The present invention provides a method for preparing a histidine and uracil double-deficient *Pichia* strain, wherein the method comprises:
(1) Performing mutagenesis on *Pichia*, and screening to obtain a uracil auxotrophic mutant;
(2) Knocking out a HIS4 gene from the uracil auxotrophic mutant obtained in step (1), and screening to obtain a histidine deficient mutant;
(3) Knocking in an exogenous gene and the HIS4 gene in the histidine deficient mutant obtained in step (2), and screening to obtain a mutant expressing the exogenous gene;
(4) Performing mutagenesis on the mutant obtained in step (3), and screening to obtain a mutant in which the exogenous gene knocked in in step (3) is not mutated but the expression of the exogenous gene is relatively higher or the activity of the expression product thereof is relatively higher; and
(5) Knocking out the HIS4 gene knocked in in step (3) from the mutant obtained in step (4), and screening to obtain a histidine deficient mutant; and optionally,
(6) Knocking out the URA3 gene in the histidine deficient mutant obtained in step (5), and screening to obtain a histidine and uracil double-mutated mutant.

The present invention also provides a method for preparing a *Pichia* strain for expressing an exogenous gene, wherein the method comprises:
(1) Performing mutagenesis on *Pichia*, and screening to obtain a uracil auxotrophic mutant;
(2) Knocking out a HIS4 gene from the uracil auxotrophic mutant obtained in step (1), and screening to obtain a histidine deficient mutant;
(3) Knocking in an exogenous gene and the HIS4 gene in the histidine deficient mutant obtained in step (2), and screening to obtain a mutant expressing the exogenous gene;
(4) Performing mutagenesis on the mutant obtained in step (3), and screening to obtain a mutant in which the exogenous gene knocked in in step (3) is not mutated but the expression of the exogenous gene is relatively higher or the activity of the expression product thereof is relatively higher; and
(5) Knocking out the HIS4 gene knocked in in step (3) from the mutant obtained in step (4), and screening to obtain a histidine deficient mutant; and optionally,
(6) Knocking out the URA3 gene in the histidine deficient mutant obtained in step (5), and screening to obtain a histidine and uracil double-mutated mutant;
(7) Knocking in a growth promoting gene and the URA3 gene in the double mutant obtained in step (6), and screening to obtain a histidine deficient mutant; and
(8) Knocking in a vacuolar protease A gene and the URA3 gene in the double mutant obtained in step (6), and screening to obtain a histidine deficient mutant.

The present invention also provides use of the *Pichia pastoris* strain described herein in the construction of a strain expressing an exogenous gene.

The *Pichia* mutant strain of the present invention is an effective general host for exogenous expression, and can efficiently express various proteins, especially phospholipases and lipases.

DETAILED DESCRIPTION

Figure 1:
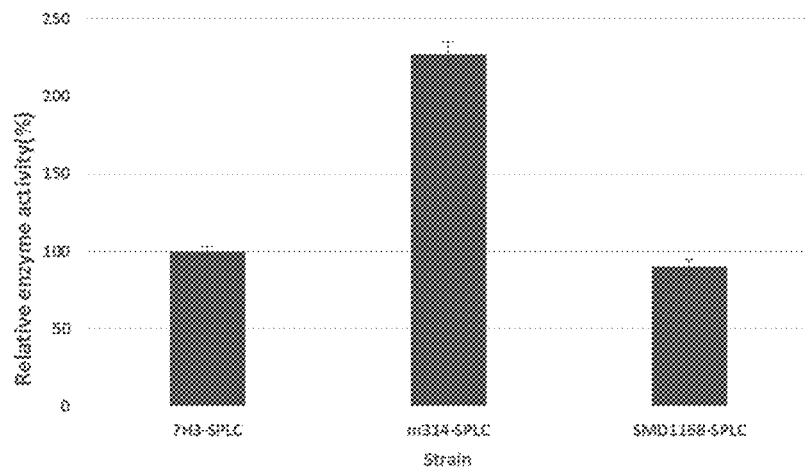
FIG. 1: Comparison figure of PLC enzyme activity of the PLC expressed by m314-SPLC.

It should be understood that, within the scope of the present invention, the above-mentioned technical features of the present invention and the technical features specifically described in the following (such as the Examples) can be combined with each other to form preferred technical solutions.

Definition

The term "genetic engineering" used in the present invention is also called gene splicing technology and DNA recombination technology. It is theoretically based on molecular genetics, and uses modern methods of molecular biology and microbiology as means to construct hybrid DNA molecules with genes from different sources in vitro according to pre-designed blueprints. Then the hybrid DNA molecules are introduced into living cells to change the original genetic characteristics of organisms, obtain new varieties, and produce new products.

The term "mutagenesis" used in the present invention has a general meaning in the art, which refers to artificial measures to induce variations in the hereditary genes of strains, and then select new and excellent varieties from the mutated strains as required. There are physical and chemical factors commonly used in mutagenesis breeding. Physical factors such as various rays, microwaves or lasers are used to treat mutagenesis materials, which are customarily called radiation breeding; chemical factors are the use of some chemical drugs that can lead to changes in genetic material—mutagen treatment of mutagenic material to induce variations, often called chemical mutagenesis.

The term "mutant" used in the present invention refers to a *Pichia* strain derived from the yeast strain CICC32806 and comprising modifications or changes, that is, substitutions, insertions and/or deletions at one or more positions. *Pichia* strain mutants can be obtained by various techniques well known in the art. In particular, examples of techniques for altering the sequence of the yeast strain CICC32806 include, but are not limited to, site-directed mutagenesis, random mutagenesis, and genetic engineering.

The terms "homology" and "identity" used in the present invention describe the degree of similarity between two or more amino acid sequences. The percentage of "sequence identity" between two sequences is determined in the following way: The two best aligned sequences are compared in the comparison window so that the part of the sequence in the comparison window can include additions or deletions (gaps) compared with the reference sequence (which does not contain additions or deletions). Thus, the optimal alignment of the two sequences can be performed. The percentage is calculated by the following: determining the number of positions where the same amino acid residue appears in the two sequences to get the number of matching positions, dividing the number of matching positions by the total number of positions in the comparison window, and multiplying the result by 100 to get the percentage of sequence identity. A sequence that is the same at each position compared with the reference sequence is considered same as the reference sequence, and vice versa.

The term "gene knockout" as used in the present invention refers to a technique for introducing an exogenous DNA, which uses a DNA fragment comprising a certain known sequence to undergo homologous recombination with a gene with the same or similar sequence in the genome of the recipient cell, so that it integrates into the genome of the recipient cell and is expressed. It is directed to a sequence with a known sequence but an unknown function, changes the gene of an organism, makes the function of a specific gene lose its effect, so that part of the function is blocked, and can further affect the organism, and then infer the biological function of the gene.

In the present invention, *Pichia* were subjected to mutagenesis, and then auxotrophic mutants were screened out, thereby *Pichia* strains for expressing exogenous genes were obtained. Specifically, the present invention used CICC32806 purchased from China Center of Industrial Culture Collection (CICC) as the starting strain. After ultraviolet mutagenesis, the uracil auxotrophic strain U7 was obtained by screening. Then through gene knockout, the HIS4 gene in U7 strain was inactivated, and histidine auxotrophic strain 7H3 was obtained. Then the PLC coding sequence was transferred into the 7H3, and the recombinant *Pichia* 7H3-SPLC was obtained by screening. The present invention further performed mutagenesis on 7H3-SPLC, and obtained mutant m314-SPLC by screening. By knocking out the PLC gene and HIS4 gene from m314-SPLC, the m314H strain was obtained. Furthermore, a histidine knockout vector could be constructed and transferred into the strain m314H of the present invention. The strain was screened in a medium comprising YNB and histidine, a medium comprising YNB and uracil, and a medium comprising YNB, histidine and uracil. The screened strain which could only grow in the medium comprising YNB, histidine and uracil was the histidine and uracil double auxotrophic strain, named as strain m314HU. Further, the present invention also overexpressed three growth promoting genes in the m314HU strain and knocked in the URA3 gene to construct the strain m315H. In addition, the present invention overexpressed the vacuolar protease A gene in the m314HU strain and knocked in the URA3 gene to construct the strain m316H.

Complete gene sequencing was performed by Suzhou GENEWIZ Biotechnology Co., Ltd. After the genome of the strain was extracted by GENEWIZ, it was interrupted and filled in, and the 3' end was added with A and then ligated with a linker comprising the Index sequence. The sequencing library constructed according to this strategy was bridged to a sequencing chip and then subjected to Illumina Hiseq sequencing. After the re-sequenced off-machine data were processed, the original data were obtained, filtered to remove linkers, decontaminated, and then compared with a reference genome. Through the comparison of results, repetitive sequences caused by PCR amplification in each library were removed, and then the sequencing depth and degree of coverage, single nucleotide variation (SNV), insertion/deletion (InDels) etc. relative to the reference genome were calculated. For reference gene sets and SNV data sets, some standard biological information analysis such as mutation annotation and functional enrichment could also be performed. The coverage rate of 99.99% and above, the average depth of 400× and above and the depth distribution of more than 200× accounted for more than 99.95%. Through sequencing, in M314H, M315H, and M316H, compared with GS115 or CICC32806, at least differences at the following 6 sites were comprised. The gene encoding sequence carried the above sites and the gene function annotations are as follows:

BQ9382_C1-2260, 308EKKdel, a hypothetical protein, wherein BQ9382_C1-2260 is the number given by GENEBANK, wherein C1: the first chromosome, 2260 is the gene number, and EKK at positions 308-310 are deleted (SEQ ID NO:21, encoded by SEQ ID NO:27).

BQ9382_C1-3800, E129K, 60S ribosomal subunit assembly/export protein LOC1. BQ9382_C1-3800 is the number given by GENEBANK, wherein C1: the first chromosome, 3800 is the gene number, and E at position 129 is mutated to K (SEQ ID NO:22, encoded by SEQ ID NO:28).

BQ9382_C1-5700, I312M, mitochondrial external NADH dehydrogenase, class II NAD(P)H: quinone oxidoreductase. BQ9382_C1-5700 is the number given by GENEBANK, wherein C1: the first chromosome, 5700 is the gene number, and I at position 312 is mutated to M (SEQ ID NO:23, encoded by SEQ ID NO:29).

BQ9382_C2-3950, Q145X, an essential protein, having a binding partner Psr1p and used for completely activating a general stress. BQ9382_C2-3950 is the number given by GENEBANK, wherein C2: the second chromosome, 3950 is the gene number, and Q at position 145 changes to the stop codon (SEQ ID NO:24, encoded by SEQ ID NO:30).

BQ9382_C3-2220, E188K, hypothetical protein. BQ9382_C3-2220 is the number given by GENEBANK, wherein C3: the third chromosome, and 2220 is the gene number (SEQ ID NO:25, encoded by SEQ ID NO:31).

BQ9382_C3-4370, W196x, orotidine 5'-phosphate decarboxylase. BQ9382_C3-4370 is the number given by GENEBANK, wherein C3: the 3rd chromosome, 4370 is the gene number, and W at position 196 is mutated to a stop codon (SEQ ID NO:26, encoded by SEQ ID NO:32).

Those of ordinary skill in the art can use strategies including but not limited to homologous recombination, gene knockout and complementation, zinc finger nuclease, TALE nuclease, Crisp/Cas9, etc., to introduce one or the above six mutations disclosed in the present invention into a *Pichia* strain of interest.

In the present invention, the mutagenesis can be physical mutagenesis or chemical mutagenesis. Physical mutagenesis includes ultraviolet mutagenesis, such as placing the *Pichia* strain under ultraviolet light for a period of time, for example, 60 to 120 seconds. Chemical mutagenesis involves contacting the *Pichia* strain with a chemical mutagen such as nitrosoguanidine for a period of time, for example, 15 to 60 minutes.

In the present invention, a medium comprising uracil and 5-fluoroorotic acid (5-FOA), such as a medium comprising YNB (yeast nitrogen source without ammonia), can be used to cultivate the mutagenized strains, and uracil deficient strains can be obtained by screening. For example, in some embodiments, the mutagenized strains can be cultured in a medium comprising YNB, glycerol, agarose, uracil and 5-fluoroorotic acid, and cultured at 25-33° C. in the dark for 3-8 days. Then, single colonies grown in this medium can be picked out and transferred into a medium comprising YNB and uracil (such as comprising YNB, glycerol, agarose and uracil). Strains which can only grow on this medium can be picked up to obtain uracil-deficient strains. In these media, the concentration of YNB can be 10-20 g/L, the content of glycerol can be 0.5-2%, the content of agarose can be 1-3%, the concentration of uracil can be 30-100 μg/mL, and if any, the concentration of 5-FOA can be 0.5-1.2 mg/mL.

In certain embodiments, the present invention uses a *Pichia* with the deposit number CICC32806 as the starting strain for mutagenesis. Therefore, in these embodiments, the uracil-deficient strain is a strain obtained from a *Pichia* with the deposit number CICC32806 after mutagenesis and screening for uracil auxotrophy.

The obtained uracil-deficient strains can be knocked out its histidine dehydrogenase gene (HIS4) by gene knockout method, and screened in a medium comprising histidine to screen out the strains which can grow in the medium comprising histidine, i.e., the histidine-deficient strains. Usually, the uracil-deficient strains in which the histidine knockout vector are transferred are cultured in a MDS screening plate comprising histidine (such as 10-50 μg/mL), and the obtained single colonies are respectively inoculated into a medium comprising YNB and a medium comprising YNB and histidine. Histidine-deficient strains can be screened out by selecting the strains that can grow in the histidine-comprising medium but cannot grow in the histidine-free medium by comparison.

In some embodiments of the present invention, the strains obtained after mutagenesis and histidine auxotrophic screening are transferred into an expression vector expressing PLC, and they are screened to obtain the mutant 7H3-SPLC, which has a large hydrolysis circle when cultured on a phospholipid plate, and in which the introduced nucleic acid sequence used to express PLC (such as AOX promoter, signal peptide, PLC gene, transcription terminator, etc.) has no mutation. Usually, when the expression vector of PLC is introduced, if the HIS4 gene is introduced at the same time, the strain thus constructed is not a histidine auxotrophic strain.

In a further embodiment, the mutant can be subjected to further physical mutagenesis, such as ultraviolet irradiation, to screen out mutant m314-SPLC, which has a large hydrolysis circle when cultured on a phospholipid plate, and in which the introduced nucleic acid sequence used to express PLC (such as AOX promoter, signal peptide, PLC gene, transcription terminator, etc.) has no mutation.

Conventional techniques can be used to knock out the previously introduced exogenous genes from the mutant m314-SPLC, including the PLC gene and the marker gene such as the HIS4 gene. For example, the strain m314H of the present invention can be obtained by constructing the AOX-His gene fragment, electro-transforming the mutant m314-SPLC, culturing on a histidine-comprising phospholipase screening plate, selecting the transformants without a hydrolysis circle, streaking on a histidine-free plate and a histidine-comprising plate respectively, and selecting transformants with the correct phenotype (growing on the histidine-comprising plate but not growing on the histidine-free plate). It should be understood that various mutants obtained in the process of constructing this strain, such as the mutants described above, are also included in the protection scope of the present invention.

The strain m314H of the present invention was deposited at China General Microbiological Culture Collection Center (CGMCC, No. 1 West Beichen Road, Chaoyang District, Beijing 100101) on Oct. 31, 2018, and was classified and named as *Pichia pastoris* with the deposit number of CGMCC No. 16670.

In certain embodiments, the present invention also includes histidine and uracil double auxotrophic strains. Specifically, a histidine knockout vector can be constructed and transferred into the strain m314H of the present invention. After screening in a medium comprising YNB and histidine, a medium comprising YNB and uracil, and a medium comprising YNB, histidine and uracil, the strain which can only grow in the medium comprising YNB, histidine and uracil can be screen out. It is the histidine and uracil double auxotrophic strain, named as m314HU.

A growth promoting gene can be introduced into the strain m314HU and the URA3 gene can be knocked in to construct a strain expressing the growth promoting gene. Herein, the growth promoting gene is preferably a growth promoting gene derived from the yeast itself, including but not limited to Protein required general stress response (Genbank no: XM_002491428.1 (SEQ ID NO:18)), Mitochondrial external NADH dehydrogenase (Genbank no: XM_002490375.1 (SEQ ID NO:19)), vacuolar protease A (Genbank no: XM_002493288.1 (SEQ ID NO:20)). One or more of the growth promoting genes can be transferred. The present invention also includes single-histidine-deficient strains in which the growth promoting gene have been successfully introduced. In certain embodiments, the single histidine deficient strain obtained in the present invention is named as strain m315H herein.

The strain m315H of the present invention was deposited at China General Microbiological Culture Collection Center (CGMCC, No. 1 West Beichen Road, Chaoyang District, Beijing 100101) on Oct. 31, 2018, and was classified and named as *Pichia pastoris* with the deposit number of CGMCC No. 16669.

The vacuolar protease A (Genbank no: XM_002493288.1 (SEQ ID NO: 20)) was introduced into the strain m314HU, and the URA3 gene was knocked in to construct a single histidine-deficient strain overexpressing the vacuolar protease A gene. In certain embodiments, the single histidine deficient strain obtained in the present invention is named as strain m316H herein.

The strain m316H of the present invention was deposited at China General Microbiological Culture Collection Center (CGMCC, No. 1 West Beichen Road, Chaoyang District, Beijing 100101) on Dec. 19, 2019, and was classified and named as *Pichia pastoris* with the deposit number of CGMCC No. 19221.

The auxotrophic *Pichia* of the present invention, especially the strains m314H, m314HU, m315H and m316H, can be used as basic strains to construct host strains for expressing exogenous genes. Herein, an exogenous gene refers to a gene of interest that is introduced into a host strain from outside, regardless of whether the gene is from another species or exists in the host genome. The exogenous gene can be a gene encoding any protein of interest. The protein of interest includes, but is not limited to, various proteins used in the fields of industry, feed or food, including but not limited to various lipases, proteases, cellulases, amylases, phytases, esterases, pectinases, galactosidases and phospholipases. In particular, in certain embodiments, the histidine auxotrophic *Pichia* described herein can be used to construct a strain expressing exogenous phospholipase C. Preferably, the amino acid sequence of the phospholipase is an amino acid sequence that has at least 80%, 90%, 95%, 98% or 99% identity with SEQ ID NO: 2; or is an amino acid sequence encoded by a polynucleotide sequence which hybridizes with SEQ ID NO: 1, the cDNA sequence thereof or the full-length complement thereof under a high stringency condition. In some embodiments, the amino acid sequence of the phospholipase C is shown in SEQ ID NO: 2. Preferably, the encoding sequence thereof is shown in SEQ ID NO: 1. In certain embodiments, the histidine auxotrophic *Pichia* described herein can be used to construct a strain expressing an exogenous lipase. Preferably, the amino acid sequence of the lipase is an amino acid sequence that has at least 80%, 90%, 95%, 98% or 99% identity with SEQ ID NO: 7 or 9; or an amino acid sequence encoded by a polynucleotide sequence which hybridizes with SEQ ID NO: 6 or 8, the cDNA sequence thereof or the full-length complement thereof under a high stringency condition. The term "high stringency condition" means a condition under which a so-called specific hybrid is formed, and a non-specific hybrid is not formed. An example of high stringency conditions include typical washing conditions for Southern hybridization, that is, washed once, preferably twice or three times at the salt concentrations and temperatures corresponding to 1×SSC, 0.1% SDS at 60° C., preferably 0.1× SSC, 0.1% SDS at 60° C., more preferably 0.1×SSC, 0.1% SDS at 68° C. In some embodiments, the amino acid sequence of the lipase is as shown in SEQ ID NO: 7 or 9, and its encoding sequence is preferably as shown in SEQ ID NO: 6 or 8. Alternatively, in certain embodiments, the strains of the present invention can be used to express a phospholipase C or lipase C whose amino acid sequence has one or more (for example, within 10) amino acid residue mutations compared with SEQ ID NO: 2, 7 or 9, including substitutions, insertions or deletions of one or more amino acid residues. Preferably, the above-mentioned substitutions, insertions or deletions of one or more amino acids are conservative mutations that maintain the normal function of the protein (that is, the activity of the mutant phospholipase C or lipase does not substantially change). A typical example of conservative mutations is a conservative substitution wherein if the substitution site is an aromatic amino acid, the substitution occurs among Phe, Trp, and Tyr; if it is a hydrophobic amino acid, the substitution occurs among Leu, Ile, and Val; If it is a polar amino acid, the substitution occurs between Gln and Asn; if it is a basic amino acid, it occurs among Lys, Arg, and His; if it is an acidic amino acid, it occurs between Asp and Glu; and if it is an amino acid with a hydroxyl group, the substitution occurs between Ser and Thr. Examples of substitutions considered to be conservative substitutions particularly comprise substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile, or Leu for Met. In addition, such amino acid residue substitutions, deletions, insertions or additions include naturally occurring mutations (mutants or variants) caused by individual differences or species differences of the bacteria from which the genes are derived.

Conventional backbone vectors for expressing exogenous genes in *Pichia* can be used to construct expression vectors suitable for the present invention for transforming the histidine auxotrophic *Pichia* described herein. Such backbone vectors include but are not limited to pPIC3, pPIC9, pPIC9k, PHIL-D1, pAO804, pAO815 and pPSC3K etc., Typical *Pichia* expression vectors comprise the alcohol oxidase-1 (AOX1) gene promoter and transcription terminator (5'AOX1 and AOXTT), which are separated by a multiple cloning site (MCS), where exogenous genes can be inserted. Such vectors can also comprise histidine alcohol dehydrogenase gene (HIS4) selection marker and 3'AOX1 region. When this kind of vector is transformed into *Pichia*, the 5'AOX1, AOXTT, 3'AOX1 and HIS4 of the vector can recombine with homologous genes on the chromosome individually or together, so that the whole vector together with the exogenous genes to be expressed can be inserted into the chromosome of the recipient, and the exogenous genes are expressed under the control of the 5'AOX1 promoter. Researchers in the art are well-known that the AOX1 promoter can be replaced. Suitable promoters include but are not limited to inducible and constitutive promoters.

The construction methods for vectors are well known in the art. For example, after the target gene is obtained by PCR amplification, the PCR product and the backbone vector are digested with corresponding restriction enzymes, and the digested fragments of the PCR product are linked with the digested fragments of the vector by a DNA ligase, and the linked product is transferred into *Escherichia coli*. After being cultured in a suitable medium, a commercially available plasmid extraction kit is used to extract a plasmid for transforming the histidine auxotrophic *Pichia* described herein.

The transformation methods of *Pichia* are also well known in the art. For example, the constructed expression vector is digested with restriction enzymes to obtain a linearized vector. Then, according to the standard transformation method (Shixuan Wu & Geoffrey J Letchworth, 2004), the competent cells of *Pichia* can be transformed by electroporation, and then coated on a suitable plate (such as MDS screening plate) and cultured for several days. Afterwards, the transformants are picked to a suitable plate, and the required recombinant strains are selected according to the biological activity of the exogenous protein expressed. For example, in certain embodiments, the exogenous protein is a phospholipase (such as phospholipase C), and the transformant will be cultured on a phospholipid plate. Generally, the phospholipid plate comprises 1 to 3% YNB, 1 to 3% phospholipids, and 1 to 3% agar. Since phospholipase can hydrolyze phospholipids, the activity of phospholipase expressed by the transformants can be determined according to the size of the hydrolysis circle. Picking the transformant with relatively large hydrolysis circle can obtain the excellent histidine auxotrophic *Pichia*.

Therefore, in certain embodiments, the present invention also includes histidine auxotrophic *Pichia* comprising the exogenous gene to be expressed. The exogenous gene is usually integrated into the genome of the *Pichia*. The histidine auxotrophic *Pichia* comprising the exogenous gene can stably express the exogenous gene. In certain embodiments, the exogenous gene is an encoding sequence for a phospholipase or lipase. In certain embodiments, the exogenous gene is an encoding sequence for phospholipase C, RML lipase, or TL lipase. In certain embodiments, the histidine auxotrophic *Pichia* has been transformed with an expression vector comprising an exogenous gene constructed with pPIC9. In some embodiments, the expression vector comprising the exogenous gene constructed with pPIC9 comprises the nucleotide sequence shown in SEQ ID NO: 1, 6 or 8. The histidine auxotrophic *Pichia* herein can be cultured using conventional culture media and methods in the art. For example, the medium may be a conventional BMGY medium. It can be cultured at 28-32° C. and 180-300 rpm. When inducing the expression of the exogenous gene, a certain amount of methanol can be added to the culture medium to induce expression. After the induction of expression, the fermentation broth is centrifuged and the supernatant is filtered to obtain the fermentation broth comprising the target protein expressed by the exogenous gene. The fermentation broth can be further concentrated by conventional methods.

In some embodiments, during fermentation, the initial medium in the upper tank can be a basic fermentation medium, which comprises calcium sulfate, potassium dihydrogen phosphate, anhydrous magnesium sulfate, ammonium sulfate, emulsified silicone oil defoamer and glycerin, and added with PTM, namely copper sulfate pentahydrate, sodium iodide, manganese sulfate monohydrate, sodium molybdate dihydrate, cobalt chloride hexahydrate, zinc chloride pentahydrate, ferrous sulfate heptahydrate, boric acid, concentrated sulfuric acid and biotin. The concentration or content of the components in the basic fermentation medium is well known in the art. For example, the concentration of calcium sulfate can be 0.5~1.5 g/L, the concentration of potassium dihydrogen phosphate can be 30~40 g/L, the concentration of anhydrous magnesium sulfate can be 10~13 g/L, the concentration of ammonium sulfate can be 6~12 g/L, the concentration of the emulsified silicone oil defoamer can be 0.1~0.5 ml/L, and the concentration of glycerin can be 30~70 g/L. In PTM, the concentration of copper sulfate pentahydrate can be 5~6.5 g/L, the concentration of sodium iodide can be 60~100 mg/L, the concentration of manganese sulfate monohydrate can be 2.0~4.0 g/L, the concentration of sodium molybdate dihydrate can be 0.2~0.4 g/L, the concentration of cobalt chloride hexahydrate can be 0.4~ 0.6 g/L, the concentration of zinc chloride pentahydrate can be 18~22 g/L, the concentration of ferrous sulfate heptahydrate can be 60~70 g/L, the concentration of boric acid can be 0.01~0.03 g/L, the concentration of concentrated sulfuric acid can be 19.0~19.5 ml/L, and the concentration of biotin can be 0.3~0.5 g/L.

Glycerin, PTM, a defoamer and ammonia are added during the growth phase of the cells. When the fermentation reaches a certain stage, for example, when the wet weight of the cells reaches 200-220 g/L, the glycerin feeding is stopped. After a period of starvation period, methanol is added for fermentation. During the addition of methanol for fermentation to induce the expression of the exogenous gene, the pH, temperature, dissolved oxygen and methanol flow rate of the fermentation process can be adjusted as required. Researchers in the art are well known that *Pichia* can also use constitutive promoters, such as GAP promoter, TEF promoter, etc., Corresponding promoters and corresponding fermentation conditions are used.

The fermentation broth can be subjected to centrifugal treatment or plate and frame filtration treatment to remove the cells, and the supernatant is subjected to microfiltration and ultrafiltration treatment, and is subjected to buffer replacement and concentration. Further, an appropriate protective agent can be added. After the appropriate protective agent is completely dissolved, the solution is stored at 4° C. as an enzyme preparation.

Therefore, the present application also provides an enzyme preparation, which comprises the fermentation broth of the *Pichia* strain comprising the exogenous gene encoding the enzyme described in any of the embodiments herein or the lysate of the cells obtained by fermentation, or the concentrate of the fermentation broth or lysate. In some preferred embodiments, the *Pichia* strain comprises an expression vector comprising the encoding sequence of the enzyme constructed with pPIC9. In certain embodiments, the enzyme preparation may also comprise glycerin and a preservative. The preservative may be a conventional preservative such as potassium sorbate. The amounts of glycerin and preservatives can be conventional amounts in the art. For example, 40-70% glycerol and 0.1-0.8% potassium sorbate by weight of the enzyme preparation can be added. In certain embodiments, the enzyme preparation comprises phospholipase C or lipase.

The enzyme preparation comprising the phospholipase C described herein can be used for oil degumming. Degumming can be implemented by a conventional method, including the step of contacting the oil to be degummed with the enzyme preparation comprising the phospholipase C described herein. For example, crude oil is heated to a certain temperature (such as 50±5° C.), added with a certain amount of pure water and enzyme solution, high-speed sheared (such as 10000 r/min), and then stirred at a certain temperature (such as 750 r/min), and reacted for 1 to 5 hours. Finally, the reaction mixture can be heated to 80-90° C. and maintained for a period of time to inactivate the enzyme, and is centrifuged to obtain degummed oil.

Therefore, the application also provides a degumming method, which comprises the step of contacting the oil to be degummed with the enzyme preparation comprising phospholipase C as described herein; and use of the enzyme preparation comprising phospholipase C as described herein in the degumming of oil.

In certain embodiments, the application also relates to use of the enzyme preparation comprising phospholipase as described herein in transesterification. For example, provided herein is a transesterification method, which includes the step of contacting a reaction substrate with the enzyme preparation comprising phospholipase of the present invention.

The application also provides use of any one or more of the sequence shown in Genbank accession number XM_002491428.1 (SEQ ID NO:18), the sequence shown in Genbank accession number XM_002490375.1 (SEQ ID NO: 19), the sequence shown in Genbank accession number XM_002493288.1 (SEQ ID NO:20) and a sequence having at least 80%, preferably at least 90%, preferably at least 95%, preferably at least 98%, preferably at least 99% identity with XM_002491428.1 (SEQ ID NO:18), XM_002490375.1 (SEQ ID NO:19) or XM_002493288.1 (SEQ ID NO:20), or the expression vector thereof in improving the expression of an exogenous gene in a host cell, or use thereof in promoting the growth of a host cell comprising an exogenous gene, or use thereof in preparing a host cell in which the expression ability of an exogenous gene is increased or the growth ability is increased. Preferably, the sequence with certain sequence identity is also derived from yeast, more preferably from *Pichia*. Preferably, the host cell is yeast, more preferably *Pichia*, more preferably the m314H strain described herein or its histidine and uracil double deficient mutant or single histidine deficient mutant. Tools well known in the art can be used to calculate the sequence identity between two or more sequences, and these tools can come from various online tools provided by NCBI.

Hereinafter, the present invention will be explained in the form of specific embodiments. It should be understood that these embodiments are merely illustrative and do not limit the protection scope of the present invention. The methods and materials used in the examples, unless otherwise specified, are all conventional methods and materials in the art.

Example 1: Obtaining Uracil Auxotrophic *Pichia* CICC32806-U7 Strain

10 μL of CICC-32806 strain was inoculated into 10 mL YPD (2% peptone, 1% yeast powder, 1% glycerol) medium, and was cultured overnight at 30° C., 240 rpm. OD600 value of the yeast solution was checked. 200OD culture solution was pipetted, and was centrifuged at 4000 rpm at room temperature. Then the supernatant was removed, and the cells were washed twice with sterile water. Finally the yeast solution was re-suspended to the concentration of 20 OD/mL. 2 mL of the yeast solution was evenly dispersed on the surface of the petri dish, which was placed on an ultra-clean workbench under ultraviolet light for 90 seconds. 100 μL was removed and coated on YNB-Uracil-FOA (13.4 g/L YNB, 1% glycerol, 2% agarose, 50 μg/mL uracil (Uracil), 0.75 mg/mL 5-fluoroorotic acid (5-FOA)) solid medium, and was cultured at 30° C. in the dark (the whole process was operated under red light to prevent back mutation) for 7 days. Single colonies grown on the YNB-Uracil-FOA solid medium in the previous step were transferred to YNB solid medium and YNB-Uracil solid medium, and strains that could only grow on YNB-Uracil solid medium were picked to obtain the uracil auxotrophic *Pichia* CICC32806-U7 strain.

Example 2: Obtaining Histidine Deficient *Pichia* CICC32806-7H3 Strain

Using the CICC32806 genome as a template, HIS-A fragment was amplified with HIS-AF/R, HIS-B fragment was amplified with HIS-BF/R, and URA3 fragment was amplified with URA3-1F/2R. The amplified fragments were ligated into pSP72 plasmid sequentially, to construct the histidine knockout vector pHISA-URA3-HISB. The primer sequences are as follows:

```
HIS-A-F:
                                 (SEQ ID NO: 10)
5'CCGCTCGAGTCACCTCAGCCAGATCAAAGT 3';

HIS-A-R:
                                 (SEQ ID NO: 11)
5'ACATGCATGCCTTTGGACAACTCTTTCTGCC 3';

HIS-B-F:
                                 (SEQ ID NO: 12)
5'CGGGGTACCCCTGGTTGATAAAGTTGCAT 3';

HIS-B-R:
                                 (SEQ ID NO: 13)
5'GGCGAGCTCAGGTGTCTTCAAAGCGACTC 3';

URA3-1F:
                                 (SEQ ID NO: 14)
ACATGCATGCCTGCAGAAATGGGAGATAACCACC;

URA3-2R:
                                 (SEQ ID NO: 15)
CGGGGTACCACTAGTGGTTTTCTGGGGGTATTTGCTG.
```

The knockout vector was linearized with XhoI and SacI, transferred into CICC32806-U7 by electroporation, and coated on the MDS screening plate comprising histidine (20 μg/mL). The single colonies that grew out were transferred to YNB solid medium and YNB-HIS solid medium respectively. The histidine auxotrophic mutant could not grow on YNB solid medium, but could grow on YNB-HIS solid medium. The strains with the correct phenotype were again single colony streaked on YNB solid medium and YNB-HIS solid medium, and single colony strains that could only grow on YNB-HIS solid medium were picked. Finally, the histidine-deficient *Pichia* CICC32806-7H3 strain was obtained.

Example 3: Construction of Phospholipase-Producing Strain 7H3-PLC

The phospholipase PLC nucleotide sequence which was codon-optimized and was synthesized by Sangon Biotech (Shanghai) Co., Ltd is:

```
                                          (SEQ ID NO: 1)
ATGAGATTTCCTTCAATTTTTACTGCAGTTTTATTCGCAGCAT

CCTCCGCATTAGCTGCTCCAGTCAACACTACAACAGAAGATGAA

ACGGCACAAATTCCGGCTGAAGCTGTCATCGGTTACTCAGATTTA

GAAGGGGATTTCGATGTTGCTGTTTTGCCATTTTCCAACAGCACA

AATAACGGGTTATTGTTTATAAATACTACTATTGCCAGCATTGCT

GCTAAAGAAGAAGGGGTATCTCTTGAGAAAAGAGAGGCTGAAGC

TTGGTCAGCTGAGGACAAGCATAAGGAAGGTGTGAATAGTCACT

TATGGATCGTGAACCGTGCCATTGATATAATGTCTAGGAATACAA

CTCTGGTTAAGCAAGATAGAGTTGCTCAATTGAATGAATGGCGTA

CAGAGCTAGAGAATGGCATCTACGCTGCTGATTATGAAAACCCC

TATTACGATAACAGTACCTTCGCTTCTCACTTTTACGATCCAGAC

AACGGAAAGACATATATCCCATTCGCCAAGCAAGCTAAGGAGAC

TGGAGCTAAGTACTTCAAGTTGGCTGGAGAGTCATACAAGAATA

AAGACATGAAGCAGGCCTTCTTTTATCTTGGGTTGTCATTGCATT

ATTTGGGCGATGTCAACCAACCTATGCATGCCGCAAACTTTACGA

ACCTGTCCTATCCACAGGGTTTTCACTCCAAGTACGAGAACTTTG

TCGATACTATTAAAGACAACTACAAAGTTACCGATGGGAACGGA

TATTGGAATTGGAAAGGCACCAACCCTGAAGAATGGATTCACGG

TGCAGCAGTAGTTGCAAAACAGGACTACTCTGGAATTGTCAATG

ACAATACCAAAGATTGGTTTGTGAAAGCCGCAGTCTCCCAGGAA

TATGCAGATAAATGGAGAGCTGAAGTTACACCTATGACTGGTAA

ACGACTAATGGATGCCCAAAGAGTTACTGCTGGTTACATTCAATT

ATGGTTCGACACTTACGGTGACAGGTAA;
```

The amino acid sequence of PLC is:

```
                                          (SEQ ID NO: 2)
MRFPSIFTAVLFAASSALAAPVNTTTEDETAQIPAEAVIGYSDLE

GDFDVAVLPFSNSTNNGLLFINTTIASIAAKEEGVSLEKREAEAWSA

EDKHKEGVNSHLWIVNRAIDIMSRNTTLVKQDRVAQLNEWRTELE

NGIYAADYENPYYDNSTFASHFYDPDNGKTYIPFAKQAKETGAKYF

KLAGESYKNKDMKQAFFYLGLSLHYLGDVNQPMHAANFTNLSYPQ

GFHSKYENFVDTIKDNYKVTDGNGYWNWKGTNPEEWIHGAAVVA

KQDYSGIVNDNTKDWFVKAAVSQEYADKWRAEVTPMTGKRLMDA

QRVTAGYIQLWFDTYGDR.
```

Primers PLC_F:

```
                                          (SEQ ID NO: 3)
TACGTATGGTCAGCTGAGGACAAGC
```
and

PLC_R:

```
                                          (SEQ ID NO: 4)
CCTAGGTTACCTGTCACCGTAAGTGTCGAAC
``` were used to amplify the mature peptide part of PLC. PCR was performed with PrimeSTAR HS (DRR010A) DNA polymerase of Takara. The reaction system was: water 33 μL, 5×PrimeSTAR buffer 10 μL, dNTP mixture (2.5 mM each) 4 μL, primers 1 μL each, plasmid template 0.5 μL, PrimeSTAR enzyme 0.5 μL. The PCR reaction program was 30 cycles of 98° C. for 10 seconds and 68° C. for 1 minute.

The PCR product was purified by PCR product purification kit of Axygen (AP-PCR-50), digested withSnaBI and AvrII restriction endonucleases of NEB, and purified by PCR product purification kit of Axygen again. At the same time, pPIC9K plasmid was digested with the same restriction endonucleases, and the digested product was purified in the same way. UsingT4 DNA ligase of Fermentas, according to the product instructions, the digested fragments of the PCR product and the digested fragments pPIC9k vector were ligated. The ligated product was transferred into *E. coli* DH5α by heat shock method, and cultured overnight on an LB plate comprising ampicillin. The next day, a single clone was picked and cultured in LB liquid medium. The plasmid was extracted using plasmid extraction kit of Axygen and sent to Shanghai Sangon Biotech for sequencing.

The correctly sequenced recombinant expression vector was digested and linearized with Bgl II restriction endonuclease, electroporated into *Pichia* CICC32806-7H3, SMD1168 competent cell according to the standard transformation method of *Pichia* (Shixuan Wu & Geoffrey J Letchworth, 2004), streaked on the selection medium MDS screening plate and cultured at 28° C. for three days. Transformants were picked and coated on a phospholipid plate (1% YNB, 2% phospholipids, 2% agarose, 1% glycerol), and cultured at 30° C. for 2 days. Transformants with hydrolysis circles and a single copy of the phospholipase gene were picked, numbered as 7H3-SPLC and SMD1168-SPLC recombinant strains.

Example 4: Obtaining the m314-SPLC Strain by UV Mutagenesis

7H3-SPLC colonies were picked into 5 mL YPD medium, and were cultured overnight at 30° C., 240 rpm shaking table. OD600 value of the yeast solution was checked. 200OD of the yeast solution was pipetted, and was centrifuged at 4000 rpm at room temperature. Then the supernatant was removed, and the cells were washed twice with sterile water. Finally the yeast solution was re-suspended to the concentration of 20 OD/mL. 2 mL of the yeast solution was evenly dispersed on the surface of the petri dish, which was placed on an ultra-clean workbench under ultraviolet light for 90 seconds. 100 μL was removed and coated on a phospholipid plate, and was cultured at 30° C. in the incubator in the dark (the whole process was operated under red light to prevent back mutation) for 4 days. The mutant with large hydrolysis circle was picked, and the colony thereof was PCR amplified with KOD-FX enzyme and *Pichia* expression sequencing universal 5'AOX and 3'AOX primers according to the instructions for use of the enzyme. The PCR product was sent to Shanghai Sengon for sequencing. It was found that the nucleic acid part artificially transferred into the yeast, i.e., AOX promoter, signal peptide, PLC gene, transcription terminator, etc., did not have a mutation. Therefore, the change of the mutant was a mutation of the strain itself. The strain was named as m314-SPLC.

Example 5: Shaking Flask Fermentation of 7H3-SPLC, m314-SPLC and SMD1168-SPLC

According to Example 2 and Example 3, it can be seen that the amino acid sequences of the PLC genes contained in the three strains 7H3-SPLC, m314-SPLC and SMD1168-SPLC are exactly the same and the copy number is a single copy. These three strains were inoculated into 50 mL of BMGY medium, cultured overnight at 30° C. and 240 rpm, and 200 OD of cells were collected by centrifugation. The cells were re-suspending washed with sterile water twice, and then re-suspended in BMMY medium. 2% methanol was added to BMMY medium, and the expression was induced at 30° C. and 240 rpm. 0.5 mL methanol was added to 50 mL medium every 12 h. After 3 days of induction, the fermentation broth was centrifuged at 8000 rpm, 4° C., and the supernatant of the fermentation broth was taken for enzyme activity determination and protein electrophoresis detection.

pNPPC phospholipase determination method:

The definition of pNPPC method phospholipase enzyme activity unit: Under the conditions of temperature of 37° C. and pH value of 7.6, the amount of enzyme that catalyzes the release of 1 μmol of phosphocholine from the substrate in 1 minute is 1 phospholipase activity unit (U).

The preparation of reaction buffer: 0.1M boric acid-sodium borate buffer (pH 7.6), 20 mM pNPPC, 1% Triton-X-100, 1 mM CaCl$_2$).

The specific steps of the determination: Two clean centrifuge tubes were taken, one of which was used as a sample tube and the other was used as a blank control tube. 600 μL of reaction buffer was added to each centrifuge tube. 25 μL of the enzyme solution to be tested was added to the sample tube, and the blank tube was left alone. The two tubes were placed together in a 37° C. constant temperature water bath for 15 minutes, and then immediately added with 500 μL 0.5M sodium hydroxide solution to stop the reaction. 25 μL of the enzyme solution to be tested was added to the blank tube. The absorbance was measured at 405 nm. The blank tube was used to correct the zero point.

The results of enzyme activity determination are shown in FIG. 1. The results show that the phospholipase activity of m314-SPLC was increased by 127% compared with the starting strain 7H3-SPLC, and by 152% compared with SMD1168-SPLC.

Polyacrylamide gel electrophoresis analysis: 0.22 μm filter membrane was used to filter the supernatant. After the same amount of supernatant was concentrated to the same volume using a Milipore 10 KDa ultrafiltration concentration tank, the same volume of concentrated enzyme solution was taken for polyacrylamide gel electrophoresis analysis.

Figure 2:
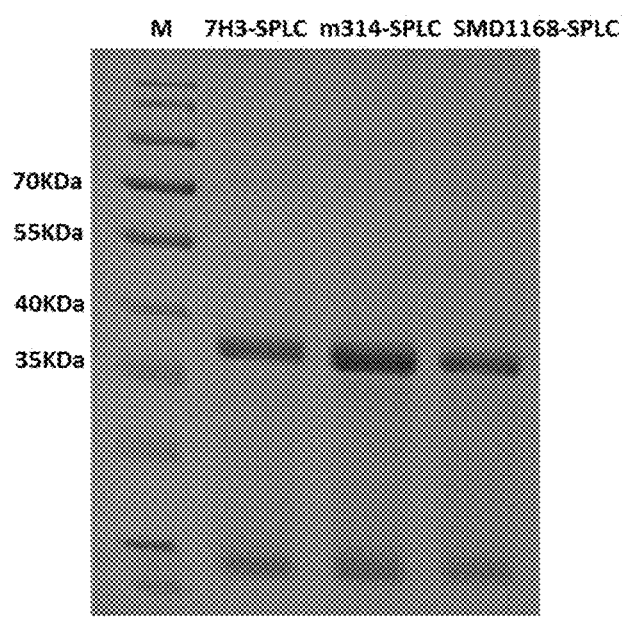
FIG. 2: Comparison figure of protein electrophoresis of the PLC expressed by m314-SPLC.

The results of electrophoresis are shown in FIG. 2. The results show that there are obvious target bands in 3 lanes, located between the 35-40 KDa bands. The target protein content in each lane is consistent with the measured phospholipase activity.

Therefore, the protein expression ability of the m314-SPLC strain obtained by UV mutagenesis increased by 127% compared with that before mutagenesis.

Example 6: Knockout of PLC Gene and his Gene from m314-SPLC Strain

The nucleotide sequence (AOX-His) used to knock out the PLC gene is as follows:

(SEQ ID NO: 5)
CTCGAGATTCAGGTGAACCCACCTAACTATTTTTAACTGGGA

TCCAGTGAGCTCGCTGGGTGAAAGCCAACCATCTTTTGTTTCGGG

GAACCGTGCTCGCCCCGTAAAGTTAATTTTTTTTCCCGCGCAGC

TTTAATCTTTCGGCAGAGAAGGCGTTTTCATCGTAGCGTGGGAAC

AGAATAATCAGTTCATGTGCTATACAGGCACATGGCAGCAGTCA

CTATTTTGCTTTTTAACCTTAAAGTCGTTCATCAATCATTAACTGA

CCAATCAGATTTTTTGCATTTGCCACTTATCTAAAAATACTTTTGT

ATCTCGCAGATACGTTCAGTGGTTTCCAGGACAACACCCAAAAA

AAGGTATCAATGCCACTAGGCAGTCGGTTTTATTTTTGGTCACCC

ACGCAAAGAAGCACCCACCTCTTTTAGGTTTTAAGTTGTGGGAAC

AGTAACACCGCCTAGAGCTTCAGGAAAAACCAGTACCTGTGACC

GCAATTCACCATGATGCAGAATGTTAATTTAAACGAGTGCCAAAT

CAAGATTTCAACAGACAAATCAATCGATCCATAGTTACCCATTCC

AGCCTTTTCGTCGTCGAGCCTGCTTCATTCCTGCCTCAGGTGCAT

AACTTTGCATGAAAAGTCCAGATTAGGGCAGATTTTGAGTTTAAA

ATAGGAAATATAAACAAATATACCGCGAAAAAGGTTTGTTTATA

GCTTTTCGCCTGGTGCCGTACGGTATAAATACATACTCTCCTCCC

CCCCCTGGTTCTCTTTTTCTTTTGTTACTTACATTTTACCGTTCCGT

CACTCGCTTCACTCAACAACAAAATAAACTAGTGGTACCGTCAGC

CACCAAAGTAGTGAATAGACCATCGGGCGGTCAGTAGTCAAAG

ACGCCAACAAAATTTCACTGACAGGGAACTTTTTGACATCTTCAG

AAAGTTCGTATTCAGTAGTCAATTGCCGAGCATCAATAATGGGG

ATTATACCAGAAGCAACAGTGGAAGTCACATCTACCAACTTTGC

GGTCTCAGAAAAAGCATAAACAGTTCTACTACCGCCATTAGTGA

AACTTTTCAAATCGCCCAGTGGAGAAGAAAAAGGCACAGCGATA

CTAGCATTAGCGGGCAAGGATGCAACTTTATCAACCAGGGTCCT

ATAGATAACCCTAGCGCCTGGGATCATCCTTTGGACAACTCTTTC

TGCCAAATCTAGGTCCAAAATCACTTCATTGATACCATTATTGTA

CAACTTGAGCAAGTTGTCGATCAGCTCCTCAAATTGGTCCTCTGT

AACGGATGACTCAACTTGCACATTAACTTGAAGCTCAGTCGATTG

AGTGAACTTGATCAGGTTGTGCAGCTGGTCAGCAGCATAGGGAA

ACACGGCTTTTCCTACCAAACTCAAGGAATTATCAAACTCTGCAA

```
CACTTGCGTATGCAGGTAGCAAGGGAAATGTCATACTTGAAGTC

GGACAGTGAGTGTAGTCTTGAGAAATTCTGAAGCCGTATTTTTAT

TATCAGTGAGTCAGTCATCAGGAGATCCTCTACGCCGGACGCATC

GTGGCCGGCATCACCGGCGCCACAGGTGCGGTTGCTGGCGCCTA

TATCGCCGACATCACCGATGGGAAGATCGGGCTCGCCACTTCG

GGCTCATGAGCGCTTGTTTCGGCGTGGGTATGGTGGCAGGCCCCG

TGGCCGGGGACTGTTGGGCGCCATCTCCTTGCATGCACCATTCC

TTGCGGCGGCGGTGCTCAACGCCTCAACCTACTACTGGGCTGCT

TCCTAATGCAGGAGTCGCATAAGGGAATTC.
```

The AOX-His gene fragment was amplified by PCR. The m314-SPLC strain was transformed by electroporation, and was coated on a phospholipase screening plate comprising histidine. The transformants without hydrolysis circle were picked and streaked on a plate without histidine and that with histidine. The transformant with the correct phenotype (growing on the plates with histidine, and not growing on the plates without histidine) was selected and named as m314H. The strain m314H was deposited at China General Microbiological Culture Collection Center (CGMCC, No. 1 West Beichen Road, Chaoyang District, Beijing 100101) on Oct. 31, 2018, and was classified and named as *Pichia pastoris* with the deposit number of CGMCC No. 16670.

Example 7: Evaluation of m314H Strain Using RML Gene as a Reporter Gene

The RML lipase gene was used to evaluate the enhancement effect of the m314H strain on the expression level of other proteins. The RML gene used was codon-optimized, and was synthesized by Sangon Biotech (Shanghai) Co., Ltd. The nucleotide sequence is:

```
                                          (SEQ ID NO: 6)
GTTCCAATCAAGAGACAATCTAATTCCACTGTCGATTCTTTG

CCTCCATTGATTCCTTCTAGAACTAGTGCACCTTCATCCTCTCCAT

CTACAACTGACCCTGAGGCTCCAGCTATGTCAAGAAATGGTCCAC

TTCCTTCTGATGTTGAGACCAAGTACGGAATGGCCCTGAATGCTA

CTTCTTATCCAGATTCTGTCGTTCAAGCTATGAAAAGAGAGGCTG

AAGCTTCCATCGACGGAGGTATTAGAGCCGCTACTTCTCAGGAA

ATCAACGAACTTACTTACTATACAACTTTGTCAGCTAATTCTTACT

GTAGAACTGTTATTCCTGGTGCTACTTGGGATTGCATACATTGTG

ACGCCACTGAAGATTTAAAGATAATTAAAACCTGGTCTACTTTGA

TTTACGACACTAACGCTATGGTTGCTAGAGGAGATTCCGAGAAG

ACTATTTATATCGTGTTTAGAGGTTCTTCATCTATTCGTAATTGGA

TCGCTGATTTGACATTCGTTCCAGTCTCTTACCCTCCAGTTTCTGG

TACTAAGGTTCACAAAGGATTTCTTGATTCTTATGGTGAAGTTCA

AAACGAGTTGGTTGCTACTGTCTTGGATCAGTTTAAACAATACCC

ATCTTATAAGGTTGCTGTCACTGGTCACTCTTTGGGAGGTGCTAC

TGCCTTGCTGTGTGCTTTAGGTTTATACCAGAGAGAGGAAGGATT

GTCTTCAAGTAACCTATTCTTGTACACTCAAGGTCAGCCTAGAGT

TGGAGATCCAGCATTTGCTAATTATGTGGTTTCTACTGGTATTCC

ATATAGACGTACTGTTAACGAAAGAGACATAGTACCACACTTGC

CTCCAGCTGCCTTCGGATTTCTGCATGCCGGTGAAGAGTACTGGA

TCACAGATAATTCTCCTGAAACCGTTCAAGTGTGTACATCTGATT

TAGAGACTTCCGACTGCTCTAACAGTATTGTTCCATTTACTTCAGT

TCTTGATCATTTGTCTTATTTTGGAATTAACACCGGTTTGTGTACT

TAA;
```

The amino acid sequence of RML is:

```
                                          (SEQ ID NO: 7)
VPIKRQSNSTVDSLPPLIPSRTSAPSSSPSTTDPEAPAMSRNGPLP

SDVETKYGMALNATSYPDSVVQAMKREAEASIDGGIRAATSQEINE

LTYYTTLSANSYCRTVIPGATWDCIHCDATEDLKIIKTWSTLIYDTN

AMVARGDSEKTIYIVFRGSSSIRNWIADLTFVPVSYPPVSGTKVHKG

FLDSYGEVQNELVATVLDQFKQYPSYKVAVTGHSLGGATALLCAL

GLYQREEGLSSSNLFLYTQGQPRVGDPAFANYVVSTGIPYRRTVNER

DIVPHLPPAAFGFLHAGEEYWITDNSPETVQVCTSDLETSDCSNSIVP

FTSVLDHLSYFGINTGLCT.
```

Primers were designed based on the synthesized RML gene sequence to construct pPIC9K-RML expression vector. After linearization with restriction endonuclease BglII, the 7H3 and m314H strains were transformed by electroporation, respectively. After selection by lipase plate, the transformants with hydrolysis circles and a single copy of RML gene were selected, numbered as 7H3-SRML and m314-SRML. The selected transformants were subjected to shaking flask fermentation (fermentation conditions were as described in Example 5). After the fermentation broth was concentrated by ultrafiltration, the same volume of concentrated enzyme solution was taken for lipase activity determination and polyacrylamide gel electrophoresis analysis.

pNPP Lipase Determination Method:

The definition of pNPP method lipase enzyme activity unit: Under the condition of temperature of 40° C. and pH value of 8.0, the amount of enzyme that catalyzes the release of 1 μmol of p-nitrophenol (pNp) from the hydrolysis of the substrate p-nitrophenyl palmitate in 1 minute is 1 enzyme activity unit (U).

Substrate buffer: 5.3 mL 0.2 mol/L $NaH_2PO_4$ solution and 94.7 mL 0.2 mol/L $Na_2HPO_4$ solution were taken, mixed and then added with about 280 mL water, added with 0.92 g sodium deoxycholate, 0.44 g arabic gum powder, stirred to dissolve, adjusted with $H3PO_4$ or NaOH to pH8.0, diluted to 400 mL, and stored at 4° C.

Substrate pNPP solution (0.0795 mol/L, 3 mg/L): 0.03 g of p-nitrophenyl palmitate (pNPP) was weighted, added with 10 mL of isopropanol, stirred to dissolve, and stored at 4° C.

Specific measurement steps: 1 mL pNPP solution and 9 mL substrate buffer solution were taken and mixed. Two clean centrifuge tubes were taken, one of which was used as a sample tube and the other was used as a blank control tube. 600 μL of reaction buffer was added to each centrifuge tube. 25 μL of the enzyme solution to be tested was added to the sample tube, and the blank tube was left alone. The two tubes were placed together in a 40° C. constant temperature water bath for 15 minutes, and then immediately added with 500 μL absolute ethanol to stop the reaction. 25 μL of the enzyme solution to be tested was added to the blank tube, and was centrifuged at 12000 rpm for 2 min. The absorbance was measured at 405 nm. The blank tube was used to correct the zero point.

Figure 3:
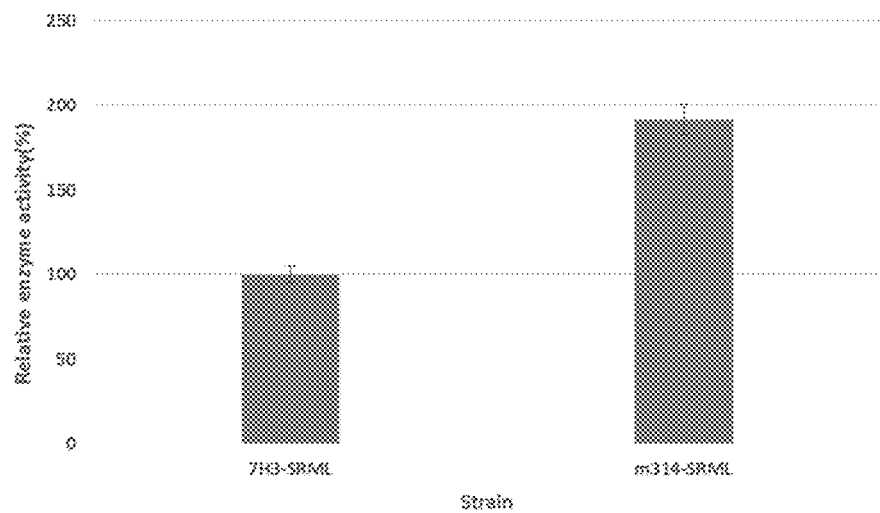
FIG. 3: Comparison figure of the enzyme activity of the RML expressed by m314H.

The results of enzyme activity determination are shown in FIG. 3. The results show that the activity of RML lipase expressed by m314-SRML was 92% higher than that of the starting strain 7H3-SRML.

Polyacrylamide gel electrophoresis analysis: 0.22 μm filter membrane was used to filter the supernatant. After the same amount of supernatant was concentrated to the same volume using a Milipore 10 KDa ultrafiltration concentration tank, the same volume of concentrated enzyme solution was taken for polyacrylamide gel electrophoresis analysis.

Figure 4:
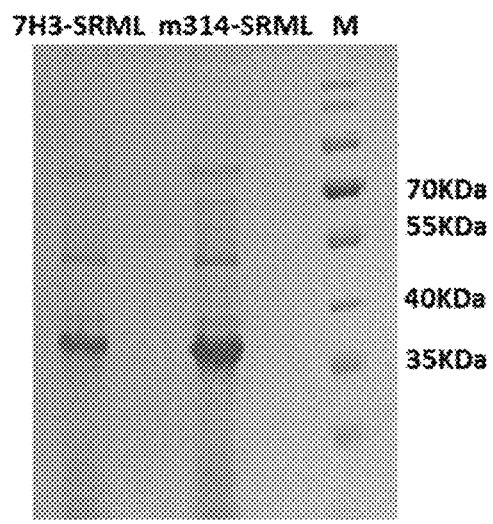
FIG. 4: Comparison figure of the protein electrophoresis of the RML expressed by m314H.

The results of electrophoresis are shown in FIG. 4. There are obvious target bands in both lanes, located between the 35-40 KDa bands. The target protein content in each lane is consistent with the measured phospholipase activity.

Summarizing the results of Example 5 and Example 7, when the m314H strain obtained by UV mutagenesis was used to express PLC and RML, its protein expression ability was increased by 127% and 92% respectively compared with the starting strain 7H3.

Example 8: Overexpression of Growth Promoting Genes in m314H Strain

Using the CICC32806 genome as a template, HIS-A fragment was amplified with HIS-AF/R, and HIS-B fragment was amplified with HIS-BF/R. The amplified fragments were ligated into pSP72 plasmid sequentially, to construct the histidine knockout vector pHISA-HISB. The knockout vector was linearized with XhoI and SacI, transformed into m314H by electroporation, and coated on the MDS screening plate comprising histidine, Uracil and 5-FOA. The single colonies that grew out were transferred to YNB-HIS solid medium, YNB-Uracil and YNB-Uracil-HIS solid medium respectively. The histidine and uracil double auxotrophic transformant was a single colony strain that could only grow on YNB-Uracil-HIS. Thus, the histidine and uracil double auxotrophic *Pichia* m314HU strain was finally obtained.

Using the CICC32806 genome as a template, the URA3 fragment was amplified with primers URA3-1F/2R. The three growth-promoting fragments, Protein required general stress response (Genbank no: XM_002491428.1 (SEQ ID NO:18)), Mitochondrial external NADH dehydrogenase (Genbank no: XM_002490375.1 (SEQ ID NO:19)) and Proteinase A (Genbank no: XM_002493288.1 (SEQ ID NO:20)), were synthesized by Sangon Biotech (Shanghai) Co., Ltd. Then these three gene fragments and URA3 fragments were respectively ligated into the pSP72 plasmid sequentially to construct the overexpression vectors pURA3-Stress, pURA3-NADH and pURA3-ProA. The knockout vector was linearized with XhoI and BglII. The three growth-promoting gene overexpression vector fragments were co-transformed into m314H by electroporation, and coated on the MDS screening plate comprising histidine. PCR verification was used to guarantee that all overexpressed genes were successfully introduced to obtain the m315H strain. The strain m315H was deposited at China General Microbiological Culture Collection Center (CGMCC, No. 1 West Beichen Road, Chaoyang District, Beijing 100101) on Oct. 31, 2018, and was classified and named as *Pichia pastoris* with the deposit number of CGMCC No. 16669.

The sequences of Genbank no: XM_002491428.1, Genbank no: XM_002490375.1 and Genbank no: XM_002493288.1 used are as follows:

>XM_002491428.1 Komagataella Phaffii GS115 Protein Required, with Binding Partner Psr1p, for Full Activation of the General Stress Response (PAS_Chr2-1_0559), Partial mRNA (SEQ ID NO: 18)
ATGAATAGCGTCATCACTCAAGTTGAAGAGAACAGGTCTGATAGCC

ATCTGTCCAGTGAAGCACAGCAGTTTGACGATGACTATAACACTGA

GATCCGGCTCAACATACGCGGAACTAGCGCAACCATTACCAGAGAT

GAACTGATGGCACTACCAGAAAGCATTCTACTGTGTTTGTTTCCCA

ACGGAGTGTTTGTAGATATCGAAGGAAATGTCATCACAAACCTTAC

AGAGGAGGATGTTGTGTACGTAAATTTCTCACCAGAGTGCTTCAAC

TATATAGTGGATACTTTCAACGAAGCAGCAGCCTCCGATATCAATA

GAGTCCACGACGAAAGGCTAGTGATCGAAGATGGTGCCGACCTGTT

GCAGAGCAAGCCTTCAGTTATCGTTCTTCGTGAGGATCTCGACTAC

TATTGTATCCCGCCCGTCCAAGGAATGAGCAAAGAACAGATGATTC

AAGTCAAAATAGAAGTTGGACATTCACTAGTCAATGAGGCACACAT

ATTTAAGGGTCTTGGCCATCAACAGAATAAGACTTTGGGTCCTGCT

GAGCAGCACCTTGCGGATATGCTGTGCTCATCGGGATTCGTTGCTG

ACGGTTGCTGGGGCCACCGGTCTTTAGAACCTGATAAGACAGTTGT

GTTCTCCCTAGCATTGGTGCGATTGAAGCCAGACAGCCCTGAAGAT

ACTACCAACACCAAGAAATCTAAATTCAACACATTGCAATACCGTA

ACTCCCGAAAAAGGCCAAAGAAAACACTACAGCCACAAAACTTC

TGCTATTTTGGAGGAAGCCAGCTCGTAAATGTTGGTGGGCCAGTGA

AATGATCAAAACCGATCTCTCAAGACTTAATTTGAAAGACAGCAAT

GGAAATCCCATTTCAACGGTGGAAATTAAAGTTCACATTAGAAGAG

TTTGGACTTTGGAGTTGTCAGTGATTGGAGTGCAATAA

>XM_002490375.1 Komagataella Phaffii GS115 Mitochondrial External NADH Dehydrogenase, a Type II NAD(P)H: Quinone Oxidoreductase (PAS_Chr1-4_0299), Partial mRNA (SEQ ID NO: 19)
ATGTTTTCTAGAAGCGCTAGGCAATTGGGTAGTGGGAGCATATTGA

GGAGTCCACTTCGTTCTGCGTTCCGTCGGGCTGCTTCTACCACCCCA

ACTACTCCAGTCCCACCACCACCCCCTCCAATTCCAGCTACTACTCC

AGTGGTTAAGAAGAAGAGAATCGGCTTTTTCCGTTTGACTTGGAGA

CTGACCTGGCTATCGTTGTTGGGTAGTGCTGCGTACTTGACTTACGA

GGTTTACAAGGAAGTCAATCCTTCTCCACAGATCCCACAAAGTCCT

CTGAAGCCAAATGGAAACCGTCGGAAAACCGTCGTCATCTTGGGTT

CCGGTTGGGGTGCAATTTCCACTTTGAAACATTTGGATACTTCCCTG

-continued
```
TACAACGTGGTCGTCGTCTCTCCAAGAAACTACTTTTGTTCACCCC
ATTGCTTCCTTCCGTTCCGACCGGAACTATCGACTTGAAATCGATTA
TAGACCCTGTGAGAACTATCGCCAAGTCAACCCCAGGTGAGGTGAC
ATATTTGGAAGCTGAGGCTACTGATATCGATATTGCTAAGAAACAA
CTGACTATCCAACATTCGTCTTACTCTGCCACTTCTGGTGTTCACCA
CGTCACTATTGGCGGAGATGAAGCCAAGCCTATTGTCGCAACTATT
GAATATGACTATCTGGTCTTCGCCATTGGTGCACAAACTGCAACCT
TCGGAATTCCAGGAATTGAGAAGTATGCCTACTACCTGAAGGAAAC
TGATGATGCTGCCAGAATCCGTCGTTCTCTGTTTGAAACCATTGAA
GCCTCTCAATTGCTTCCAAAGGACTCCGAAGAGAGAAAACGTTTGT
TGTCTGTCGTCGTCTGTGGTGGAGGCCCAACTGGCGTTGAGTTGGC
TGCCGAGATCAAGGACTACATTGATGAAGACCTTTCCAGATTTGTG
CCAGGAATTGAGAACGAAATGTCCGTTACTCTAGTCGAAGCCCTTC
CAAATGTTCTGAACGCTTTTAACCACAAGTTAATTGAGTACACTGA
GTCTATTTTTGAGAAGCAGCAATTGGACCTTAGAGTTAACACCATG
GTCAAAAGGTTGATGACAAGAACGTTTACGCTACAGTCAAGAAA
TCTGGTGGTGACACTGAAAATGTTACAATTCCATATGGAACTTTAG
TTTGGGCCACCGGTAATGGTCCTCGTCCTTTGACGAAAGCTGTTGCT
GCCCAAATTGAAGAGCAGAAAACTGCAAGAAGAGGCCTGCTTATC
GGCGAACATTTGTTAGTCGATGGCACTGACTCCGTGTTTGCCCTTGG
AGATTGTACCTTCACGAAGAACCCACCTACCGCCCAAGTTGCTCAC
CAAGAGGGTATTTATTTAGCATCTCATTTGGCCAAACTCTCCAAGA
TTGACGACCTCAAGTATGAAATTGGTCAGAACACCGATCCTGAGCA
ATTAGTCCGCTTGCAGCGCCGTTTGGACAGAACCCAAGCTTCGATT
CTGCCTTTCAAGTACACTCACCAAGGTGCTCTCGCATACATTGGTTC
CGAACGTGCTGTTGCCGATTTAGTTTGGGGTGACTGGTCCAACGTTT
CCACTGGAGGATCGCTTACGTTCCTGTTCTGGAGATCCGCCTATGTA
TCCATGATGTTGGGAGTTCGTACCAAGATTTTGGTCGTCTCTGATTG
GATCAAGGTCAAAGTCTTTGGAAGAGATTGTTCCAAGGAATAA
```
>XM_002493288.1 Komagataella Phaffii GS115 Vacuolar Aspartyl Protease (Proteinase A) (PAS_Chr3_1087), Partial mRNA (SEQ ID NO: 20)
```
ATGATATTTGACGGTACTACGATGTCAATTGCCATTGGTTTGCT
CTCTACTCTAGGTATTGGTGCTGAAGCCAAAGTTCATTCTGCTAAG
ATACACAAGCATCCAGTCTCAGAAACTTTAAAAGAGGCCAATTTTG
GGCAGTATGTCTCTGCTCTGGAACATAAATATGTTTCTCTGTTCAAC
GAACAAAATGCTTTGTCCAAGTCGAATTTTATGTCTCAGCAAGATG
GTTTTGCCGTTGAAGCTTCGCATGATGCTCCACTTACAAACTATCTT
AACGCTCAGTATTTTACTGAGGTATCATTAGGTACCCCTCCACAATC
GTTCAAGGTGATTCTTGACACAGGATCCTCCAATTTATGGGTTCCTA
```
-continued
```
GCAAAGATTGTGGATCATTAGCTTGCTTCTTGCATGCTAAGTATGA
CCATGATGAGTCTTCTACTTATAAGAAGAATGGTAGTAGCTTTGAA
ATTAGGTATGGATCCGGTTCCATGGAAGGGTATGTTTCTCAGGATG
TGTTGCAAATTGGGGATTTGACCATTCCCAAAGTTGATTTTGCTGAG
GCCACATCGGAGCCGGGGTTGGCCTTCGCTTTTGGCAAATTTGACG
GAATTTTGGGGCTTGCTTATGATTCAATATCAGTAAATAAGATTGTT
CCTCCAATTTACAAGGCTTTGGAATTAGATCTCCTTGACGAACCAA
AATTTGCCTTCTACTTGGGGGATACGGACAAAGATGAATCCGATGG
CGGTTTGGCCACATTTGGTGGTGTGGACAAATCTAAGTATGAAGGA
AAGATCACCTGGTTGCCTGTCAGAAGAAAGGCTTACTGGGAGGTCT
CTTTTGATGGTGTAGGTTTGGGATCCGAATATGCTGAATTGCAAAA
AACTGGTGCAGCCATCGACACTGGAACCTCATTGATTGCTTTGCCC
AGTGGCCTAGCTGAAATTCTCAATGCAGAAATTGGTGCTACCAAGG
GTTGGTCTGGTCAATACGCTGTGGACTGTGACACTAGAGACTCTTT
GCCAGACTTAACTTTAACCTTCGCCGGTTACAACTTTACCATTACTC
CATATGACTATACTTTGGAGGTTTCTGGGTCATGTATTAGTGCTTTC
ACCCCCATGGACTTTCCTGAACCAATAGGTCCTTTGGCAATCATTG
GTGACTCGTTCTTGAGAAAATATTACTCAGTTTATGACCTAGGCAA
AGATGCAGTAGGTTTAGCCAAGTCTATTTAG.
```

Example 9: Evaluation of m315H Strain Using TL Gene as a Reporter Gene

The TL lipase gene was used to evaluate the enhancement effect of the m315H strain on the expression level of other proteins. The TL gene used was codon-optimized, and was synthesized by Sangon Biotech (Shanghai) Co., Ltd. The nucleotide sequence is:

(SEQ ID NO: 8)
```
GAAGTCTCTCAAGACTTGTTCAACCAGTTCAACTTGTTCGCT
CAATACTCTGCCGCTGCCTACTGTGGTAAGAACAATGATGCTCCA
GCTGGTACTAACATTACCTGTACTGGTAACGCTTGTCCAGAAGTT
GAGAAGGCTGATGCTACCTTCCTGTACTCCTTCGAAGACTCTGGA
GTTGGAGATGTTACTGGTTTCCTGGCCTTGGATAACACTAACAAG
TTGATCGTTCTGTCCTTCAGAGGTTCCAGATCCATCGAGAACTGG
ATTGGTAACTTGAACTTTGACTTGAAGGAGATCAACGACATCTGT
TCTGGATGTCGTGGTCACGATGGATTTACCTCCTCTTGGAGATCT
GTTGCTGATACCTTGAGACAGAAGGTCGAAGATGCTGTCAGAGA
ACATCCAGACTATAGAGTTGTCTTCACTGGTCACTCCTTGGGAGG
TGCCTTGGCTACTGTTGCTGGTGCTGACTTGCGTGGTAATGGTTA
TGACATTGATGTCTTCTCCTACGGTGCTCCAAGAGTTGGTAATCG
TGCCTTCGCTGAGTTTCTGACCGTCCAAACTGGAGGTACTTTGTA
CAGAATTACCCATACTAACGACATTGTTCCAAGATTGCCACCACG
TGAGTTCGGATACTCTCATTCCTCTCCAGAGTACTGGATCAAGTC
```

-continued

```
TGGAACCTTGGTTCCAGTCACTCGTAACGACATCGTCAAGATTGA

AGGTATTGATGCCACTGGAGGTAACAATCAACCAAACATTCCAG

ACATTCCAGCTCACTTGTGGTACTTTGGTCTGATTGGTACTTGCTT

GTAA;
```

The TL amino acid sequence is:

```
                                       (SEQ ID NO: 9)
EVSQDLFNQFNLFAQYSAAAYCGKNNDAPAGTNITCTGNACPE

VEKADATFLYSFEDSGVGDVTGFLALDNTNKLIVLSFRGSRSIENWI

GNLNFDLKEINDICSGCRGHDGFTSSWRSVADTLRQKVEDAVREHP

DYRVVFTGHSLGGALATVAGADLRGNGYDIDVFSYGAPRVGNRAF

AEFLTVQTGGTLYRITHTNDIVPRLPPREFGYSHSSPEYWIKSGTLVP

VTRNDIVKIEGIDATGGNNQPNIPDIPAHLWYFGLIGTCL.
```

The primers were designed according to the synthesized TL gene sequence to construct pPIC9K-TL expression vector. After linearization with restriction endonuclease BglII, the 7H3, m314H and m315H strains were transformed by electroporation respectively. After screening by lipase plate, transformants having hydrolysis circles and a single copy of TL gene were selected, numbered as 7H3-STL, m314-STL and m315-ST. The selected transformants were subjected to shaking flask fermentation. After the fermentation broth was concentrated by ultrafiltration, the same volume of concentrated enzyme solution was taken, and the lipase activity determination and polyacrylamide gel electrophoresis analysis were performed by the pNPP method lipase determination method.

Figure 5:
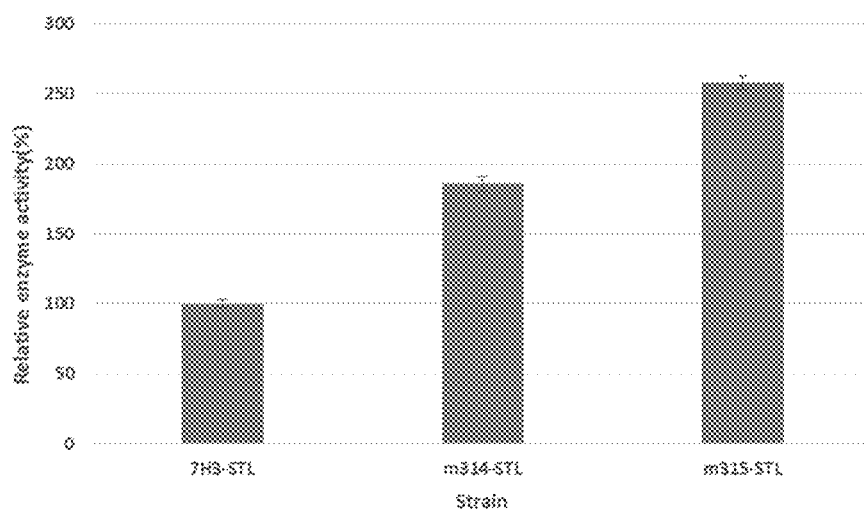
FIG. 5: Comparison figure of the enzyme activity of the TL expressed by m315H.

The results of enzyme activity determination are shown in FIG. 5. The results show that the TL lipase activity expressed by m315-STL increased by 39% compared with m314-STL.

Polyacrylamide gel electrophoresis analysis: 0.22 μm filter membrane was used to filter the supernatant. After the same amount of supernatant was concentrated to the same volume using a Milipore 10 KDa ultrafiltration concentration tank, the same volume of concentrated enzyme solution was taken for polyacrylamide gel electrophoresis analysis.

Figure 6:
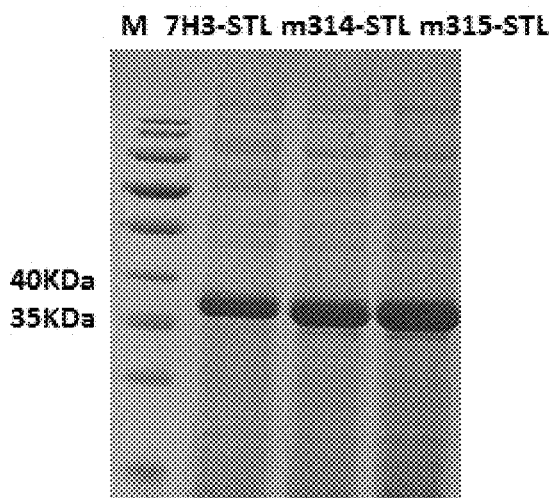
FIG. 6: Comparison figure of the protein electrophoresis of the TL expressed by m315H.

The results of electrophoresis are shown in FIG. 6. There are obvious target bands in 3 lanes, located between the 35-40 KDa bands. The target protein content in each lane is consistent with the measured TL lipase activity.

Summarizing the results of Example 5, Example 7 and Example 9, when m314H obtained by UV mutagenesis of strain 7H3 was used to express PLC, RML and TL, the protein expression ability was increased by 127%, 92% and 86% respectively compared with the staring strain 7H3, which proved that the ability of the strain m314H to express exogenous proteins was significantly higher than that of the starting strain 7H3, and it had excellent characteristics. 3 kinds of growth-promoting genes were further overexpressed in m314H, and the strain m315H was constructed. It was found that when strain m315H expressed TL, the protein expression level was further increased by 39% compared with m314H. The protein expression level of m315H was further increased.

Example 10: Overexpression of Vacuolar Protease A in the m314H Strain

Using the CICC32806 genome as a template, the URA3 fragment was amplified with primers URA3-1F/2R. The vacuolar protease A (Genbank no: XM_002493288.1 (SEQ ID NO:20)) gene fragment was synthesized by Sangon Biotech (Shanghai) Co., Ltd., and the Proteinase A gene fragment was amplified with the primers proAF: CGAGTTTCTCCGTATCTAAT (SEQ ID NO: 16) and proAR: TCCTCATCTATACCCCAGG (SEQ ID NO: 17). The amplified URA3 fragment and proteinase A fragment were co-transformed into m314HU obtained in Example 8 by electroporation. The electrotransferred material was coated on the MDS screening plate comprising histidine. PCR verification was used to guarantee that all transformed genes were successfully introduced to obtain the m316H strain. The strain m316H was deposited at China General Microbiological Culture Collection Center (CGMCC, No. 1 West Beichen Road, Chaoyang District, Beijing 100101) on Dec. 19, 2019, and was classified and named as *Pichia pastoris* with the deposit number of CGMCC No. 19221.

After genome sequencing, there are 3 copies of Proteinase A in the m316H strain, two of which are located at the original Proteinase A position of the genome, and the other copy is inserted in the BQ9382_C2-3700 gene, Subunit of the Anaphase-Promoting Complex/Cyclosome encoding region.

Example 11: Evaluation of the m316H Strain Using TL Gene as Reporter Gene

The pPIC9K-TL expression vector constructed in Example 9 was linearized by restriction endonuclease BglII and then electroporated to transform the m316H strains. After lipase plate screening, transformants with hydrolysis circles and a single copy of the TL gene were selected, numbered as m316-STL. The selected transformants were compared with 7H3-STL, m314-STL and m315-STL obtained in Example 9 in shaking flask fermentation. After the fermentation broth was concentrated by ultrafiltration, the same volume of concentrated enzyme solution was taken, and the lipase activity determination and polyacrylamide gel electrophoresis analysis were performed by the pNPP method lipase determination method.

Figure 7:
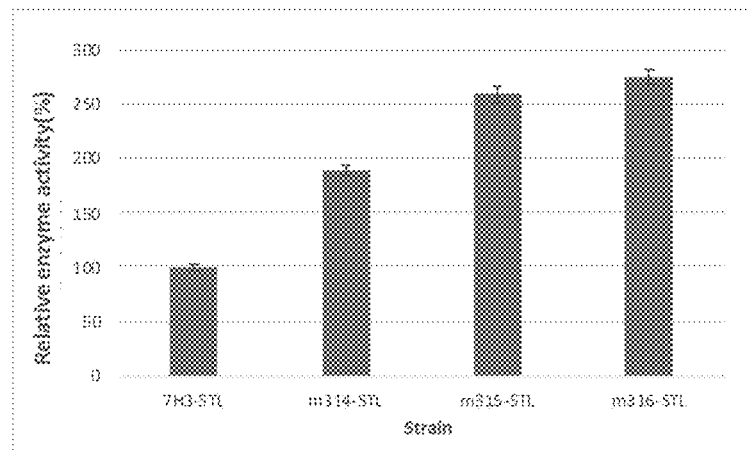
FIG. 7: Comparison figure of the enzyme activity of the TL expressed by m316H.

The results of enzyme activity determination are shown in FIG. 7. The results show that the TL lipase activity expressed by m316-STL was similar to that of m315-STL, which is 45% higher than that of m314-STL.

Polyacrylamide gel electrophoresis analysis: 0.22 μm filter membrane was used to filter the supernatant. After the same amount of supernatant was concentrated to the same volume using a Milipore 10 KDa ultrafiltration concentration tank, the same volume of concentrated enzyme solution was taken for polyacrylamide gel electrophoresis analysis.

Figure 8:
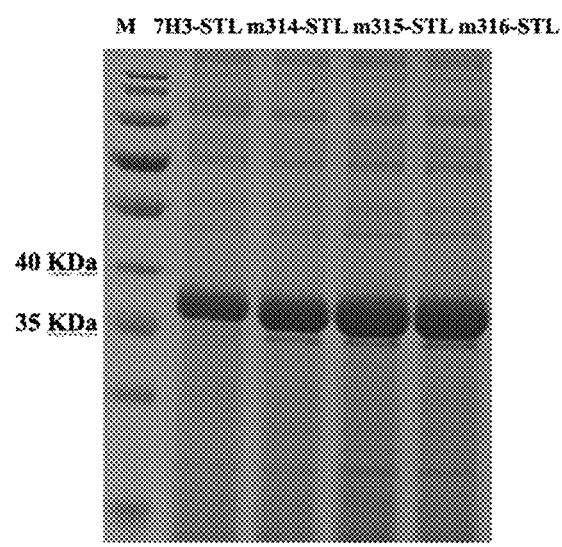
FIG. 8: Comparison figure of the protein electrophoresis of the TL expressed by m316H.

The results of electrophoresis are shown in FIG. 8. There are obvious target bands in 4 lanes, located between the 35-40 KDa bands. The target protein content in each lane is consistent with the measured TL lipase activity.

Example 12: Genome Sequencing of the *Pichia* Strains of the Present Invention and Comparison with Existing *Pichia* Genome The 32806, m314, m315 and m316 strains mentioned in the present invention were submitted to Suzhou GENEWIZ Biotechnology Co., Ltd for genome sequencing. After the genome of the strain was extracted by GENEWIZ, it was interrupted and filled in, and the 3' end was added with A and then ligated with a linker comprising the Index sequence. The sequencing library constructed according to this strategy was bridged to a sequencing chip and then subjected to Illumina Hiseq sequencing. After the re-sequenced off-machine data were processed, the original data were obtained, filtered to remove linkers, decontaminated, and then compared with a reference genome. Through the comparison of results, repetitive sequences caused by PCR amplification in each library were removed, and then the sequencing depth and degree of coverage, single nucleotide variation (SNV), insertion/deletion (InDels) etc. relative to the reference genome were calculated. For reference gene sets and SNV data sets, some standard biological information analysis such as mutation annotation and functional enrichment could also be performed. The coverage rate of 99.99% and above, the average depth of 400× and above and the depth distribution of more than 200× accounted for more than 99.95%.

After genome sequencing and comparison with the existing Pichia genome, the starting strain CICC32806 of the present invention and GS115 have 1125 SNV events and 830 INDEL events reported in the genome. Obviously, the starting strain of the present invention is significantly different from GS115. After comparison, the genomes of the m314H, m315H and m316H strains of the present invention and the GS115 or CICC32806 strains have at least the following changes in their genomes: BQ9382_C1-2260, EKK deletion at positions 308-310, a hypothetical protein (SEQ ID NO:21, encoded by SEQ ID NO:27); BQ9382_C1-3800, E129K, 60S ribosomal subunit assembly/export protein LOC1 (SEQ ID NO: 22, encoded by SEQ ID NO:28); BQ9382_C1-5700, 1312M, mitochondrial external NADH dehydrogenase, class II NAD(P)H: quinone oxidoreductase (SEQ ID NO:23, encoded by SEQ ID NO:29); BQ9382_C2-3950, Q145X, an essential protein having a binding partner Psr1p and used for completely activating a general stress response (SEQ ID NO:24, encoded by SEQ ID NO:30); BQ9382_C3-2220, E188K, a hypothetical protein (SEQ ID NO: 25, encoded by SEQ ID NO:31); and BQ9382_C3-4370, W196X, orotidine 5\'-phosphate decarboxylase (SEQ ID NO:26, encoded by SEQ ID NO: 32).

The gene and protein sequences of the above six mutations are as follows:

BQ9382_C1-2260, EKK Deletion at Positions 308-310, a Hypothetical Protein (SEQ ID NO: 21)
MPPKTPAWKKIGLKVQNEILNDPFSVEHLEGAIKTTKKRTREPVKSEPE

GSKKAPKRKKLPKSERPPPPEKDQLAYLRQFHEDRDNWKFSKQKQNW

VLRHLSVIPSEYEAALSSYLEGMQGQSRDRLVGEFKTVVERWNAFCE

QAEQKLIKQLEENVKNGQTKEEAEEKEGEDEEKETKEEIKAPEYDYVI

RASRLFNVLTGEKIYVKNVEMEEEKEEEKEGEEKDLVEEEKQENDEK

VEEIDHKHKSKDREDAEDVRDEGLSNLIVEKVEVTEFIDDTDYLDKDE

KDAEESEATNEDKQDEETEKKEKKEKKEKKEKKEKKEKKEKKEKKEK

KEKKEKKEKKKEKKERKST

Which is encoded by:

(SEQ ID NO: 27)
ATGCCCCCAAAGACCCCAGCGTGGAAGAAAATTGGCCTCAAGGTC

CAAAATGAGATTTTGAATGACCCCTTTAGTGTGGAACATTTAGAAG

GAGCTATAAAAACCACAAAGAAACGCACACGAGAGCCTGTCAAAA

GTGAGCCTGAGGGGAGTAAGAAGGCTCCAAAGAGAAAGAAGTTAC

CCAAATCAGAAAGGCCACCCCCACCAGAAAAAGATCAGCTTGCTT

ATCTTAGACAGTTTCATGAGGATAGAGATAATTGGAAATTTTCCAA

GCAGAAACAGAACTGGGTGTTGAGACACCTTTCTGTTATTCCTTCC

GAGTATGAGGCAGCTCTAAGTAGTTACCTGGAGGGAATGCAGGGG

CAATCTCGAGACCGTTTGGTTGGAGAGTTCAAAACGGTTGTAGAAC

GATGGAATGCGTTCTGTGAGCAAGCAGAGCAGAAGCTGATAAAGC

AACTTGAGGAAAACGTAAAGAACGGACAGACCAAGGAAGAGGCA

GAGGAAAAGGAAGGAGAAGATGAAGAGAAGGAGACAAAGGAAGA

GATCAAGGCTCCTGAGTATGATTATGTGATCAGAGCCAGCAGATTG

TTTAATGTTCTTACTGGAGAGAAGATATACGTGAAAAACGTCGAAA

TGGAGGAAGAGAAGGAGGAAGAGAAGGAGGGGGAAGAAAAAGAT

TTAGTAGAGGAAGAAAAACAGGAAAATGATGAAAAAGTAGAGGA

AATAGATCATAAACATAAATCAAAAGACAGGGAAGATGCAGAGGA

TGTTAGGGATGAAGGTTTGAGCAATTTAATTGTGGAGAAGGTCGAA

GTAACCGAGTTTATTGACGATACTGACTATTTGGACAAAGATGAAA

AGGACGCAGAGGAATCCGAGGCTACTAATGAAGATAAGCAGGATG

AGGAAACCGAAAAGAAGGAGAAGAAGGAGAAGAAAGAAAAGAAG

GAGAAGAAAGAAAAGAAGGAGAAGGAGAAGAAGGAGAAGAAGG

AGAAGAAGGAGAAGAAGGAGAAGAAGAAAGAAAAGAAAGAACG

AAAATCTACCTGA

BQ9382_C1-3800, E129K, 60S Ribosomal Subunit Assembly/Export Protein LOC1

(SEQ ID NO: 22)
MPRNKTQAAKKKNPENFRRSVESDVFTDSEARNRLASQPKKTAKSKV

HKQSHLEVKKEQRSVRLYGKKKPLREYTEKELHIPVLNRAIVPGVVPK

ARGKKGKKFVDDHDSVVLTRLVKQINDKKDLLNKSKLEKSORIEEIRE

LKKQEIEKKEELKKQKLDDKKQQIKSKANTARAIRRRNARELARKAK

ENADEKLTTRNIKKPIKSVSFA

Which is encoded by:

(SEQ ID NO: 28)
ATGCCTCGCAATAAGACTCAAGCTGCTAAAAAGAAGAATCCGGAA

AATTTTAGAAGATCTGTTGAATCAGATGTCTTTACTGACTCCGAAG

CTCGTAATCGGCTAGCGTCTCAACCAAAAAAAACTGCGAAATCAAA

GGTTCACAAACAGAGTCACTTGGAAGTTAAGAAAGAACAAAGATC

GGTACGGTTGTATGGAAAAAAAAAACCACTTAGAGAATATACCGA

AAAAGAACTTCATATTCCTGTATTAAACAGAGCCATAGTTCCTGGT

GTTGTTCCGAAAGCTCGAGGTAAAAAGGGAAAGAAGTTTGTGGAC

GATCACGATTCTGTCGTTTTAACCAGACTTGTCAAACAAATCAACG

ACAAAAAGGACTTGCTGAACAAGAGTAAATTAGAGAAATCACAAC

GTATTGAAGAGATCCGTGAGTTAAAGAAACAAGAAATTGAAAAAA

```
AAGAGGAGCTTAAGAAGCAAAAATTGGACGATAAGAAACAACAGA

TTAAATCGAAGGCCAATACTGCAAGAGCTATTCGAAGAAGGAACG

CCAGAGAGCTTGCCAGAAAGGCGAAGGAAAACGCTGATGAAAAAC

TAACTACTCGGAACATTAAAAAACCTATCAAATCTGTGTCATTTGC

TTAA
```

BQ9382_C1-5700, 1312M, Mitochondrial External NADH Dehydrogenase, Class II NAD(P)H: Quinone Oxidoreductase (SEQ ID NO: 23)
```
MFSRSARQLGSGSILRSPLRSAFRRAASTTPTTPVPPPPPPIPATTPVV
KKKRIGFFRLTWRLTWLSLLGSAAYLTYEVYKEVNPSPQIPQSPLKPNG
NRRKTVVILGSGWGAISTLKHLDTSLYNVVVVSPRNYFLFTPLLPSVPT
GTIDLKSIIDPVRTIAKSTPGEVTYLEAEATDIDIAKKOLTIOHSSYSA
TSGVHHVTIGGDEAKPIVATIEYDYLVFAIGAQTATFGIPGIEKYAYYL
KETDDAARIRRSLFETIEASQLLPKDSEERKRLLSVVVCGGGPTGVELA
AEIKDYIDEDLSRFVPGmENEMSVTLVEALPNVLNAFNHKLIEYTESIF
EKQQLDLRVNTMVKKVDDKNVYATVKKSGGDTENVTIPYGTLVWATGNG
PRPLTKAVAAQIEEQKTARRGLLIGEHLLVDGTDSVFALGDCTFTKNPP
TAQVAHQEGIYLASHLAKLSKIDDLKYEIGQNTDPEQLVRLQRRLDRT
QASILPFKYTHQGALAYIGSERAVADLVWGDWSNVSTGGSLTFLFWR
SAYVSMMLGVRTKILVVSDWIKVKVFGRDCSKE
```

Which is encoded by:

(SEQ ID NO: 29)
```
ATGTTTTCTAGAAGCGCTAGGCAATTGGGTAGTGGGAGCATATTGA
GGAGTCCACTTCGTTCTGCGTTCCGTCGGGCTGCTTCTACCACCCCA
ACTACTCCAGTCCCACCACCACCCCCTCCAATTCCAGCTACTACTCC
AGTGGTTAAGAAGAAGAGAATCGGCTTTTTCCGTTTGACTTGGAGA
CTGACCTGGCTATCGTTGTTGGGTAGTGCTGCGTACTTGACTTACGA
GGTTTACAAGGAAGTCAATCCTTCTCCACAGATCCCACAAAGTCCT
CTGAAGCCAAATGGAAACCGTCGGAAAACCGTCGTCATCTTGGGTT
CCGGTTGGGGTGCAATTTCCACTTTGAAACATTTGGATACTTCCCTG
TACAACGTGGTCGTCGTCTCTCCAAGAAACTACTTTTTGTTCACCCC
ATTGCTTCCTTCCGTTCCGACCGGAACTATCGACTTGAAATCGATTA
TAGACCCTGTGAGAACTATCGCCAAGTCAACCCCAGGTGAGGTGAC
ATATTTGGAAGCTGAGGCTACTGATATCGATATTGCTAAGAAACAA
CTGACTATCCAACATTCGTCTTACTCTGCCACTTCTGGTGTTCACCA
CGTCACTATTGGCGGAGATGAAGCCAAGCCTATTGTCGCAACTATT
GAATATGACTATCTGGTCTTCGCCATTGGTGCACAAACTGCAACCT
TCGGAATTCCAGGAATTGAGAAGTATGCCTACACCTGAAGGAAAC
TGATGATGCTGCCAGAATCCGTCGTTCTCTGTTTGAAACCATTGAA
GCCTCTCAATTGCTTCCAAAGGACTCCGAAGAGAGAAAACGTTTGT
TGTCTGTCGTCGTCTGTGGTGGAGGCCCAACTGGCGTTGAGTTGGC
TGCCGAGATCAAGGACTACATTGATGAAGACCTTTCCAGATTTGTG
CCAGGAATGGAGAACGAAATGTCCGTTACTCTAGTCGAAGCCCTTC
CAAATGTTCTGAACGCTTTTAACCACAAGTTAATTGAGTACACTGA
GTCTATTTTTGAGAAGCAGCAATTGGACCTTAGAGTTAACACCATG
GTCAAAAAGGTTGATGACAAGAACGTTTACGCTACAGTCAAGAAA
TCTGGTGGTGACACTGAAAATGTTACAATTCCATATGGAACTTTAG
TTTGGGCCACCGGTAATGGTCCTCGTCCTTTGACGAAAGCTGTTGCT
GCCCAAATTGAAGAGCAGAAAACTGCAAGAAGAGGCCTGCTTATC
GGCGAACATTTGTTAGTCGATGGCACTGACTCCGTGTTTGCCCTTGG
AGATTGTACCTTCACGAAGAACCCACCTACCGCCCAAGTTGCTCAC
CAAGAGGGTATTTATTTAGCATCTCATTTGGCCAAACTCTCCAAGA
TTGACGACCTCAAGTATGAAATTGGTCAGAACACCGATCCTGAGCA
ATTAGTCCGCTTGCAGCGCCGTTTGGACAGAACCCAAGCTTCGATT
CTGCCTTTCAAGTACACTCACCAAGGTGCTCTCGCATACATTGGTTC
CGAACGTGCTGTTGCCGATTTAGTTTGGGGTGACTGGTCCAACGTTT
CCACTGGAGGATCGCTTACGTTCCTGTTCTGGAGATCCGCCTATGTA
TCCATGATGTTGGGAGTTCGTACCAAGATTTTGGTCGTCTCTGATTG
GATCAAGGTCAAAGTCTTTGGAAGAGATTGTTCCAAGGAATAA
```

BQ9382_C2-3950, Q145X, an Essential Protein Having a Binding Partner Psr1p and Used for Completely Activating a General Stress Response (SEQ ID NO: 24)
```
MNSVITQVEENRSDSHLSSEAQQFDDDYNTEIRLNIRGTSATITRDELM
ALPESILLCLFPNGVFVDIEGNVITNLTEEDVVYVNFSPECFNYIVDTE
NEAAASDINRVHDERLVIEDGADLLQSKPSVIVLREDLDYYCIPPV
```

Which is encoded by:

(SEQ ID NO: 30)
```
ATGAATAGCGTCATCACTCAAGTTGAAGAGAACAGGTCTGATAGCC
ATCTGTCCAGTGAAGCACAGCAGTTTGACGATGACTATAACACTGA
GATCCGGCTCAACATACGCGGAACTAGCGCAACCATTACCAGAGAT
GAACTGATGGCACTACCAGAAAGCATTCTACTGTGTTTGTTTCCCA
ACGGAGTGTTTGTAGATATCGAAGGAAATGTCATCACAAACCTTAC
AGAGGAGGATGTTGTACGTAAATTTCTCACCAGAGTGCTTCAAC
TATATAGTGGATACTTTCAACGAAGCAGCAGCCTCCGATATCAATA
GAGTCCACGACGAAAGGCTAGTGATCGAAGATGGTGCCGACCTGTT
GCAGAGCAAGCCTTCAGTTATCGTTCTTCGTGAGGATCTCGACTAC
TATTGTATCCCGCCCGTCTAA
```

BQ9382_C3-2220, E188K, a Hypothetical Protein (SEQ ID NO: 25)
MAPHPSSILFGVQEGYQLTAVSLKSNIATKYVLNNELISGLLHLTQESF
NGDTNVDFTKINPSLATDPQHYEEWSKILQKQVDALEKEQDLPDSTYQ
ELESLDNDIANLEREYLTRYKLDSKLEEDKDKQPIRELVALNDQILTRF
QTKYHKYVYEVTGDLNTVPHVTVVTDKGEVQESTQPEEDEDKDVEDT
TPQEYPSNTYYRIQKRLVF Which is encoded by (SEQ ID NO:31)
ATGGCTCCTCATCCGTCATCGATCTTGTTTGGGGTCCAAGAGGGCT
ATCAGCTGACAGCAGTGTCTCTCAAATCAAACATAGCAACCAAATA
TGTGCTTAATAATGAGTTAATTTCCGGTTTATTGCATCTCACGCAGG
AATCTTTCAACGGGGACACCAACGTTGACTTTACCAAGATCAATCC
TTCCCTGGCAACGGATCCCCAACATTATGAAGAATGGAGCAAAATA
TTACAGAAGCAAGTTGATGCACTGGAGAAGGAACAAGACCTACCA
GATTCCACCTACCAAGAGCTTGAATCTCTCGACAATGACATTGCCA
ATCTGGAAAGGGAATATCTCACGAGATACAAACTTGATTCTAAACT
TGAGGAGGACAAAGATAAACAACCTATTCGGGAACTGGTCGCACT
CAACGATCAGATACTGACAAGATTCCAAACCAAATATCACAAGTAC
GTCTACGAAGTCACGGGAGACTTGAATACCGTACCGCATGTCACGG
TCGTCACAGACAAAGGCGAAGTTCAGGAATCAACACAGCCAGAGG
AGGACGAGGATGAAGATGTAGAAGACACAACGCCCCAAGAGTATC
CAAGCAACACATACTACCGGATTCAAAAACGCTTAGTTTTCTAG BQ9382_C3-4370, W196X, Orotidine 5'-Phosphate Decarboxylase (SEQ ID NO: 26)
MARSYAERANTHQSPVARRLFALMEQKQSNLCASVDVRTTKELLELL
DKLGPFICLAKTHIDIIDDFTYDGTILPLLELSKKHKFLIFEDRKFADI
GNTVKHQYQGGVYKIAQWADITNAHGVIGSGIVKGLKEAATETTDQPRG
LLMLAELSSKGSIAHGKYTEETVEIAKSDKEFVIGFIAQNSMGGODEGF
D Which is encoded by (SEQ ID NO: 32)
ATGGCTCGCAGTTATGCCGAGAGAGCAAATACTCATCAATCACCTG
TGGCACGACGACTGTTTGCGCTTATGGAACAGAAACAGAGTAACCT
ATGCGCATCAGTCGACGTGAGAACAACTAAAGAATTATTGGAGCTT
CTAGATAAATTGGGCCCATTTATCTGTTTGGCCAAGACTCATATCG
ACATAATTGATGACTTCACGTATGATGGAACTATTCTGCCTTTATTG
GAACTATCAAAGAAACACAAGTTTTTAATTTTTGAGGACAGAAAGT
TTGCTGATATAGGCAACACTGTCAAGCATCAATATCAAGGAGGTGT
CTACAAGATTGCACAATGGGCAGATATTACAAATGCTCATGGTGTC
ATTGGTAGTGGAATTGTAAAGGGTCTAAAGGAGGCAGCCACTGAG
ACAACAGATCAACCAAGGGGACTATTGATGTTGGCTGAACTGTCGT
CAAAGGGATCAATTGCCCATGGTAAGTACACCGAAGAAACTGTAG
AAATTGCAAAATCAGACAAGGAATTCGTCATTGGGTTTATTGCTCA
AAATTCTATGGGAGGACAAGATGAAGGGTTCGATTGA

---

The invention claimed is:

1. A *Pichia* strain, which comprises genes encoding all of SEQ ID NOs: 21-26.

2. The *Pichia* strain of claim 1, wherein the *Pichia* strain is a *Pichia pastoris* strain with a deposit number of CGMCC No. 16670, a *Pichia pastoris* strain with a deposit number of CGMCC No. 16669, and a *Pichia pastoris* strain with a deposit number of CGMCC No. 19221.

3. A *Pichia pastoris* strain with the deposit number of CGMCC No. 16670.

4. A *Pichia* strain, wherein the *Pichia* strain is obtained by genetic engineering or mutagenesis of the *Pichia pastoris* strain of claim 3, and (a) is a histidine-deficient strain; and/or (b) comprises a plasmid expressing a growth promoting factor, and/or integrates an encoding sequence of a growth promoting factor in the genome, and/or expresses a growth promoting factor.

5. A *Pichia* strain, wherein the *Pichia* strain is obtained by genetic engineering or mutagenesis of the *Pichia pastoris* strain of claim 3, and (a) is a histidine-deficient strain; and/or (b) comprises a plasmid expressing vacuolar protease A gene, and/or integrates an encoding sequence of vacuolar protease A gene in the genome, and/or expresses vacuolar protease A gene.

6. A *Pichia* strain obtained by genetic engineering or mutagenesis, wherein the *Pichia* strain is obtained by genetic engineering or mutagenesis of the *Pichia* strain of claim 1, wherein the genetic engineering makes the *Pichia* strain comprise an exogenous gene or a vector comprising the exogenous gene, wherein the exogenous gene is an encoding sequence of a protein used in the field of industry, feed or food, wherein the protein is a lipase or a phospholipase, wherein the amino acid sequence of the lipase is an amino acid sequence having at least 90%, 95%, 98%, 99% or 100% identity with SEQ ID NO: 7 or 9 and wherein the activity of the mutant lipase does not substantially change, and wherein the amino acid sequence of the phospholipase is an amino acid sequence having at least 90%, 95%, 98%, 99% or 100% identity with SEQ ID NO: 2 and wherein the activity of the mutant phospholipase does not substantially change.

7. A culture comprising the *Pichia* strain according to claim 1, and optionally, a culture medium.

8. An enzyme preparation, wherein the enzyme preparation comprises fermentation broth of the *Pichia* strain according to claim 6 comprising an exogenous gene encoding the enzyme, lysate of the cells obtained by fermentation, or concentrate of said fermentation broth or lysate, wherein the enzyme is a lipase or a phospholipase, wherein the amino acid sequence of the lipase is an amino acid sequence having at least 90%, 95%, 98%, 99% or 100% identity with SEQ ID NO: 7 or 9 and wherein the activity of the mutant lipase does not substantially change, and wherein the amino acid sequence of the phospholipase is an amino acid sequence having at least 90%, 95%, 98%, 99% or 100% identity with SEQ ID NO: 2 and wherein the activity of the mutant phospholipase does not substantially change.

9. A method for transesterification or oil degumming, comprising contacting a reaction substrate of transesterification or contacting oil to be degummed with the enzyme preparation of claim 8, wherein the enzyme preparation comprises a lipase or a phospholipase, wherein the amino acid sequence of the lipase is an amino acid sequence having at least 90%, 95%, 98%, 99% or 100% identity with SEQ ID NO: 7 or 9 and wherein the activity of the mutant lipase does not substantially change, and wherein the amino acid sequence of the phospholipase is an amino acid sequence having at least 90%, 95%, 98%, 99% or 100% identity with SEQ ID NO: 2 and wherein the activity of the mutant phospholipase does not substantially change.

10. A method for constructing a strain for expressing an exogenous gene, comprising introducing the exogenous gene into the *Pichia* strain of claim 1, wherein the exogenous gene encodes a lipase or a phospholipase, wherein the amino acid sequence of the lipase is an amino acid sequence having at least 90%, 95%, 98%, 99% or 100% identity with SEQ ID NO: 7 or 9 and wherein the activity of the mutant lipase does not substantially change, and wherein the amino acid sequence of the phospholipase is an amino acid sequence having at least 90%, 95%, 98%, 99% or 100% identity with SEQ ID NO: 2 and wherein the activity of the mutant phospholipase does not substantially change.

11. The *Pichia* strain according to claim 4, wherein said growth promoting factor is a growth promoting gene derived from the yeast itself, and comprises a sequence selected from the group consisting of SEQ ID NO:18, SEQ ID NO:19 and SEQ ID NO: 20.

12. The culture of claim 7, wherein the medium is a seed medium or a fermentation medium.

13. The culture of claim 7, wherein the medium is YPD medium or BMMY medium.

14. The enzyme preparation of claim 8, wherein the *Pichia* strain comprises an expression vector comprising an encoding sequence of an enzyme, which is constructed with a pPIC9K plasmid as a backbone vector, wherein the enzyme is a lipase or a phospholipase, wherein the amino acid sequence of the lipase is an amino acid sequence having at least 90%, 95%, 98%, 99% or 100% identity with SEQ ID NO: 7 or 9 and wherein the activity of the mutant lipase does not substantially change, and wherein the amino acid sequence of the phospholipase is an amino acid sequence having at least 90%, 95%, 98%, 99% or 100% identity with SEQ ID NO: 2 and wherein the activity of the mutant phospholipase does not substantially change.

* * * * *